US011484729B2

(12) United States Patent
Cortese et al.

(10) Patent No.: US 11,484,729 B2
(45) Date of Patent: Nov. 1, 2022

(54) OPTICAL RELAY STATION-BASED IMPLANTABLE SENSOR MODULES

(71) Applicant: Cornell University, Ithaca, NY (US)

(72) Inventors: Alejandro J. Cortese, Ithaca, NY (US); Jesse H. Goldberg, Ithaca, NY (US); Teja Pratap Bollu, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/594,407

(22) PCT Filed: Apr. 15, 2020

(86) PCT No.: PCT/US2020/028374
§ 371 (c)(1),
(2) Date: Oct. 14, 2021

(87) PCT Pub. No.: WO2020/214743
PCT Pub. Date: Oct. 22, 2020

(65) Prior Publication Data
US 2022/0143418 A1    May 12, 2022

Related U.S. Application Data

(60) Provisional application No. 62/834,299, filed on Apr. 15, 2019.

(51) Int. Cl.
*A61N 5/06* (2006.01)
*G08C 23/04* (2006.01)

(52) U.S. Cl.
CPC ......... *A61N 5/0601* (2013.01); *A61N 5/0622* (2013.01); *G08C 23/04* (2013.01);
(Continued)

(58) Field of Classification Search
CPC ............... A61N 5/0601; A61N 5/0622; A61N 2005/0612; A61N 2005/0626;
(Continued)

(56) References Cited

U.S. PATENT DOCUMENTS 7,988,688 B2   8/2011   Webb et al.
8,357,187 B1   1/2013   Bendett et al.
(Continued)

FOREIGN PATENT DOCUMENTS

| EP | 0377547 A1 | 7/1990 |
|---|---|---|
| RU | 2333526 C1 | 9/2008 |
| WO | 2019042553 A1 | 3/2019 |

OTHER PUBLICATIONS

Lee, Sunwoo, et al. "A 330μm×90μm opto-electronically integrated wireless system-on-chip for recording of neural activities." 2018 IEEE International Solid-State Circuits Conference-(ISSCC). IEEE, 2018. DOI: 10.1109/ISSCC.2018.8310299 (Year: 2018).*
(Continued)

*Primary Examiner* — Jonathan T Kuo
(74) *Attorney, Agent, or Firm* — Perkins Coie LLP

(57) ABSTRACT

The technology disclosed can be implemented to construct devices with an array of optical elements to provide power to stimulate a biological process in a nerve system in living objects, and to provide patterned light outputs from the array of optical elements to indicate a corresponding electrical pattern monitored from the biological process in the nerve system. In one aspect a nerve stimulator apparatus is disclosed including a plurality of optical to electrical transducers arranged in a two-dimensional array, wherein each of the plurality of optical to electrical transducers is configured to convert light to an electrical signal; a plurality of electrodes, each electrode associated with one or more associated optical to electrical transducers; and a plurality of electrical interconnects to connect each of the plurality of electrodes to the one or more associated optical transducers. In another aspect nerve sensor apparatus is disclosed including a plurality of optical to electrical transducers; a plurality of optical sources; a plurality of electrodes, each electrode associated with one or more optical to electrical transducers, (Continued)

each optical source configured to modulate light output according to a voltage at one of the plurality of electrodes; and a plurality of electrical interconnects.

24 Claims, 21 Drawing Sheets

(52) U.S. Cl.
CPC ............... *A61N 2005/0612* (2013.01); *A61N 2005/0626* (2013.01); *A61N 2005/0647* (2013.01); *G08C 2201/40* (2013.01)

(58) Field of Classification Search
CPC ....... A61N 2005/0647; A61N 5/06–2005/073; G08C 23/04; G08C 2201/40
See application file for complete search history.

(56) References Cited

U.S. PATENT DOCUMENTS

| | | | |
|---|---|---|---|
| 9,186,060 B2 | 11/2015 | De Graff et al. | |
| 9,907,496 B1* | 3/2018 | Okandan | A61B 5/24 |
| 11,052,260 B2* | 7/2021 | Doguet | A61N 1/3605 |
| 2004/0146235 A1 | 7/2004 | Lyons | |
| 2008/0221645 A1* | 9/2008 | Kennedy | A61B 5/6846 977/950 |
| 2010/0016732 A1 | 1/2010 | Wells et al. | |
| 2014/0046408 A1 | 2/2014 | Shoham et al. | |
| 2015/0209586 A1 | 7/2015 | Silva et al. | |
| 2019/0090801 A1 | 3/2019 | Rogers et al. | |
| 2020/0206514 A1* | 7/2020 | Doguet | A61N 1/0551 |
| 2021/0133528 A1* | 5/2021 | Cortese | H04B 10/116 |

OTHER PUBLICATIONS

S. Lee, A. et al. "A 250 μm×57 μm Microscale Opto-electronically Transduced Electrodes (MOTEs) for Neural Recording," in IEEE Transactions on Biomedical Circuits and Systems, vol. 12, No. 6, pp. 1256-1266, Dec. 2018, doi: 10.1109/TBCAS.20 (Year: 2018).*
Cortese, Alejandro J., et al. "Microscopic sensors using optical wireless integrated circuits." Proceedings of the National Academy of Sciences 117.17 (2020): 9173-9179. doi: 10.1073/pnas.1919677117. (Year: 2020).*
International Search Report and Written Opinion for PCT/US20/028374, dated Apr. 15, 2020, 12 pages.

* cited by examiner

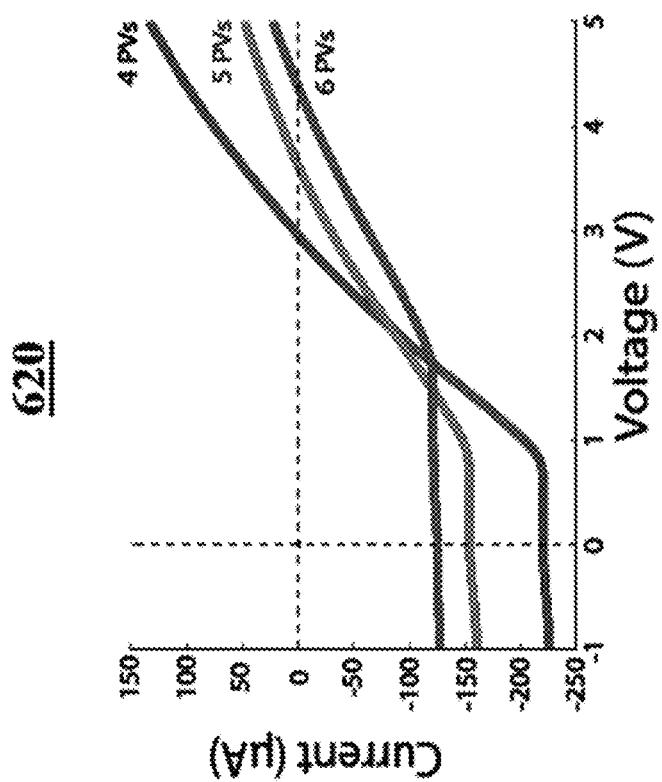
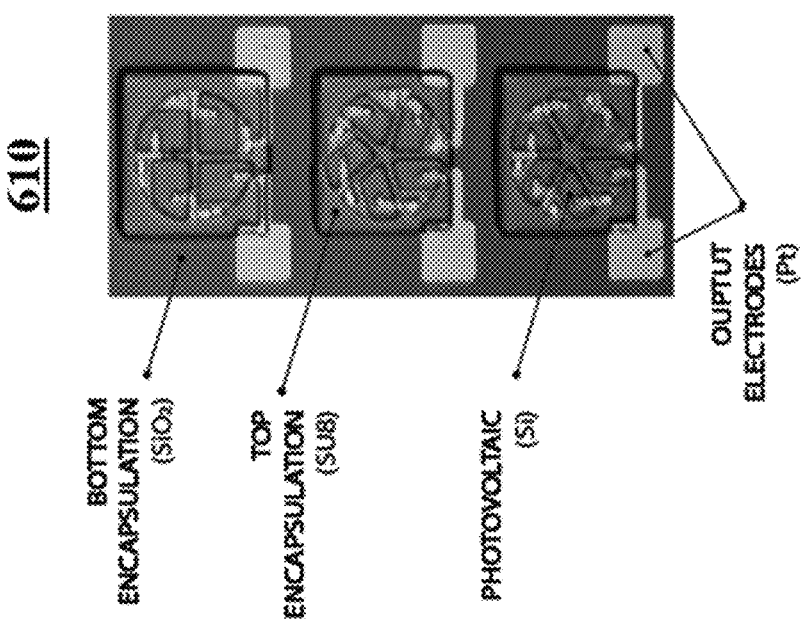
FIG. 6A

OPTICAL RELAY STATION-BASED IMPLANTABLE SENSOR MODULES

PRIORITY CLAIM AND CROSS-REFERENCE TO RELATED APPLICATION

This patent document is a 371 National Phase Application of PCT Application No. PCT/US2020/028374 entitled "OPTICAL RELAY STATION-BASED IMPLANTABLE SENSOR MODULES" filed on Apr. 15, 2020, which claims priority to and benefits of U.S. Provisional Appl. No. 62/834,299, entitled "OPTICAL RELAY STATION-BASED IMPLANTABLE ELECTRONICS" and filed on Apr. 15, 2019. The entire content of the before-mentioned patent application is incorporated by reference as part of the disclosure of this document.

TECHNICAL FIELD

The technology disclosed in this patent document relates to sensors and devices for various applications, including monitoring and stimulation of functions in biological tissue.

BACKGROUND

There is a growing interest and need for monitoring biological processes in the body making use of electronic sensors. These sensors are employed with the hope of remedying illnesses and improving quality of life with larger and larger scope of applications. Examples of such situations include recording neural activity in the brain for brain machine interfaces (BMIs), monitoring neural activity to localize the origin of epileptic seizures, monitoring muscle activity in the body to understand atrophy and degenerative muscle disease, and monitoring glucose levels in blood and sweat for patients with diabetes. Furthermore, with the growing ability of sensors to monitor these and other biological functions real-time, additional attempts are now being made to stimulate biological processes. Examples of stimulation include deep-brain stimulation (DBS) as a method to reduce Parkinson's disease tremors, microstimulation of the retina to allow for vision in the visually impaired, and electrical muscle stimulation to restore motor function.

SUMMARY

The technology disclosed in this patent document can be implemented to construct devices with an array of optical elements to provide power to stimulate a biological process in a nerve system in living objects, and to provide patterned light outputs from the array of optical elements to indicate a corresponding electrical pattern monitored from the biological process in the nerve system. As illustrated by specific examples disclosed herein, the disclosed technology can be implemented to provide fabrication methods and devices that enable implantable devices that are electrically connected to an optical relay station, which is optically powered and optically transmit monitored information.

In an embodiment of the disclosed technology, an apparatus includes a plurality of optical elements arranged in an array, each of the plurality of optical elements that are configured to perform conversion between electrical signals and optical signals, and a plurality of electrodes coupled in communication with the plurality of optical elements, each of the plurality of electrodes including an active electrode area coupled to be in communication with one of the plurality of optical elements to stimulate a biological process in a nerve system interacting with the plurality of electrodes based on electrical input signals received by the plurality of electrodes from the optical elements to produce responsive electrical signals and monitor the biological process by transmitting the responsive electrical signals from the plurality of electrodes to the plurality of optical elements which produce optical output signals based on the responsive electrical signals as monitored information. The electrical output signals are converted to patterned light outputs by the plurality of optical elements such that the patterned light outputs in the array indicate a corresponding electrical pattern monitored from the biological process in the nerve system.

In another embodiment of the disclosed technology, an apparatus includes a plurality of optical to electrical transducers arranged in a two-dimensional array, wherein each of the plurality of optical to electrical transducers is configured to convert incident light to an electrical signal, a plurality of electrodes, wherein each of the plurality of electrodes is associated with one of the plurality of optical to electrical transducers, wherein the plurality of optical to electrical transducers are configured to cause generation of electrical signals at associated electrodes, respectively, when the plurality of optical to electrical transducers is illuminated by a two-dimensional pattern of incident light so that the generated electrical signals at the associated electrodes are representative of a spatial pattern in the two-dimensional pattern of incident light, and a plurality of electrical interconnects coupled to provide electrical connection between the plurality of electrodes and the plurality of optical to electrical transducers.

In another embodiment of the disclosed technology, an apparatus includes a plurality of optical to electrical transducers arranged in a two-dimensional array, wherein each of the plurality of optical to electrical transducers is configured to convert incident light to an electrical signal, a plurality of optical sources each operable to emit light as an optical output representing a sensor measurement, wherein each optical to electrical transducer has a corresponding optical source, a plurality of electrodes, wherein each electrode is associated with one or more optical to electrical transducers from the plurality of optical to electrical transducers, wherein each corresponding optical source is configured and coupled to be modulated by a voltage at one of the plurality of electrodes, and a plurality of electrical interconnects coupled to provide electrical connection between the plurality of electrodes and the plurality of optical sources to allow for modulation of optical outputs of plurality of optical sources in response to voltages at the plurality of electrodes to produce the optical output representing the sensor measurement.

In another embodiment of the disclosed technology, an apparatus includes a plurality of optical elements arranged in an array, each of the plurality of optical elements being configured to perform conversion between electrical signals and optical signals, and a plurality of electrodes, each of the plurality of electrodes including active electrode areas mapped to at least one of the plurality of optical elements to stimulate a biological process in a nerve system based on electrical input signals received from the optical elements and monitor the biological process to transmit optical output signals as monitored information to the optical element. The electrical output signals are converted to patterned light outputs by the plurality of optical elements such that the patterned light outputs in the array indicate a corresponding electrical pattern monitored from the biological process in the nerve system.

In another embodiment of the disclosed technology, a nerve stimulator apparatus includes a plurality of optical to electrical transducers arranged in a two-dimensional array, wherein each of the plurality of optical to electrical transducers is configured to convert incident light to an electrical signal, a plurality of electrodes, wherein each of the plurality of electrodes is associated with one of the plurality of optical to electrical transducers, wherein the plurality of optical to electrical transducers are configured to generate electrical pulses at the associated electrode upon being illuminated by a two-dimensional pattern of light, and a plurality of electrical interconnects to directly connect each of the plurality of electrodes to the associated one of the one or more of the plurality of optical to electrical transducers.

In another embodiment of the disclosed technology, a nerve sensor apparatus includes a plurality of optical to electrical transducers arranged in a two-dimensional array, wherein each of the plurality of optical to electrical transducers is configured to convert incident light to an electrical signal, a plurality of optical sources, wherein each optical to electrical transducer has a corresponding optical source, a plurality of electrodes, wherein each electrode is associated with one or more optical to electrical transducers from the plurality of optical to electrical transducers, wherein each corresponding optical source is configured to be modulated by a voltage at one of the plurality of electrodes, and a plurality of electrical interconnects to directly connect each of the plurality of electrodes to a control signal configured to modulate an optical output of the corresponding optical source according to the voltage at the one of the plurality of electrodes.

BRIEF DESCRIPTION OF THE DRAWINGS

FIG. 6A shows an optical voltage amplifier fabricated on an SOI substrate and the corresponding current-voltage characteristics under illumination. Responses for 4, 5, and 6 microscale photovoltaics connected in series are shown. Components of the optical element are labeled.

DETAILED DESCRIPTION

Better understanding and control of biological functions is enabled by minimally invasive recording and stimulation devices with high channel-counts. Various methods of accomplishing high-channel count stimulation and recordings are in use and under development. Optical techniques involving genetically modified proteins such as genetically encoded calcium indicators GCaMP for recording and optogenetics for stimulation are used in research settings. Electronic techniques such as silicon microelectrodes for recording and stimulation have made progress in clinical settings.

The technology disclosed in this patent document can be implemented to construct devices with opto-electronic circuitry for sensing and identification applications, and to provide untethered devices for deployment in living objects and other applications. As illustrated by specific examples disclosed herein, a wireless sensing device with opto-electronic circuitry can be constructed to convert light into electricity for powering the sensing device which interacts with a biological issue or target substance to perform sensing measurements. The opto-electronic circuitry can be implemented to further generate output light that is modulated to carry information of the performed sensing measurement by device without requiring any physical connection to the device.

Also disclosed are examples of methods and devices that allow for high-channel count monitoring and stimulation using an optical relay station.

Figure 1A:
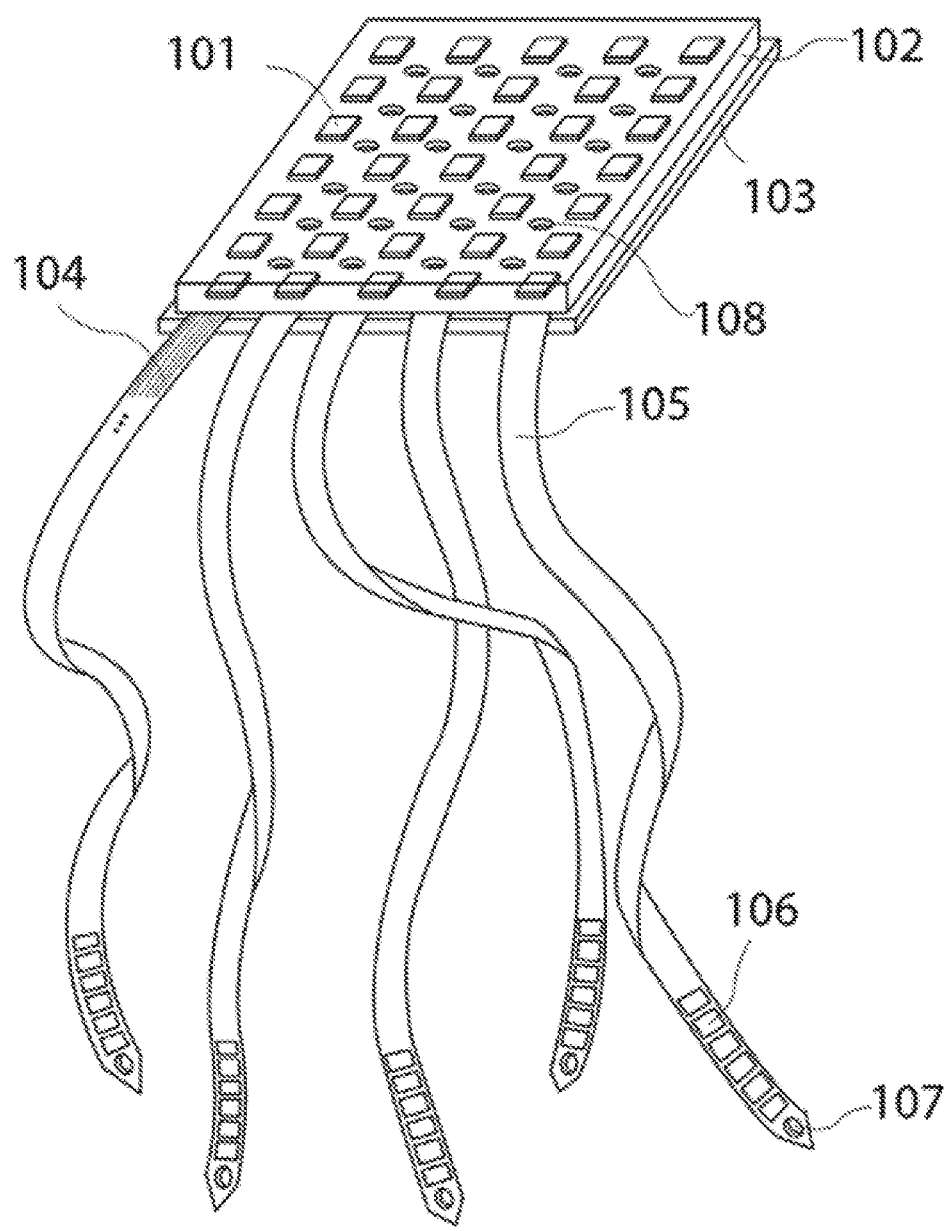
FIG. 1A illustrates an example optical relay station (ORS)-based implantable electronic device implemented based on some embodiments of the disclosed technology.
Figure 1B:
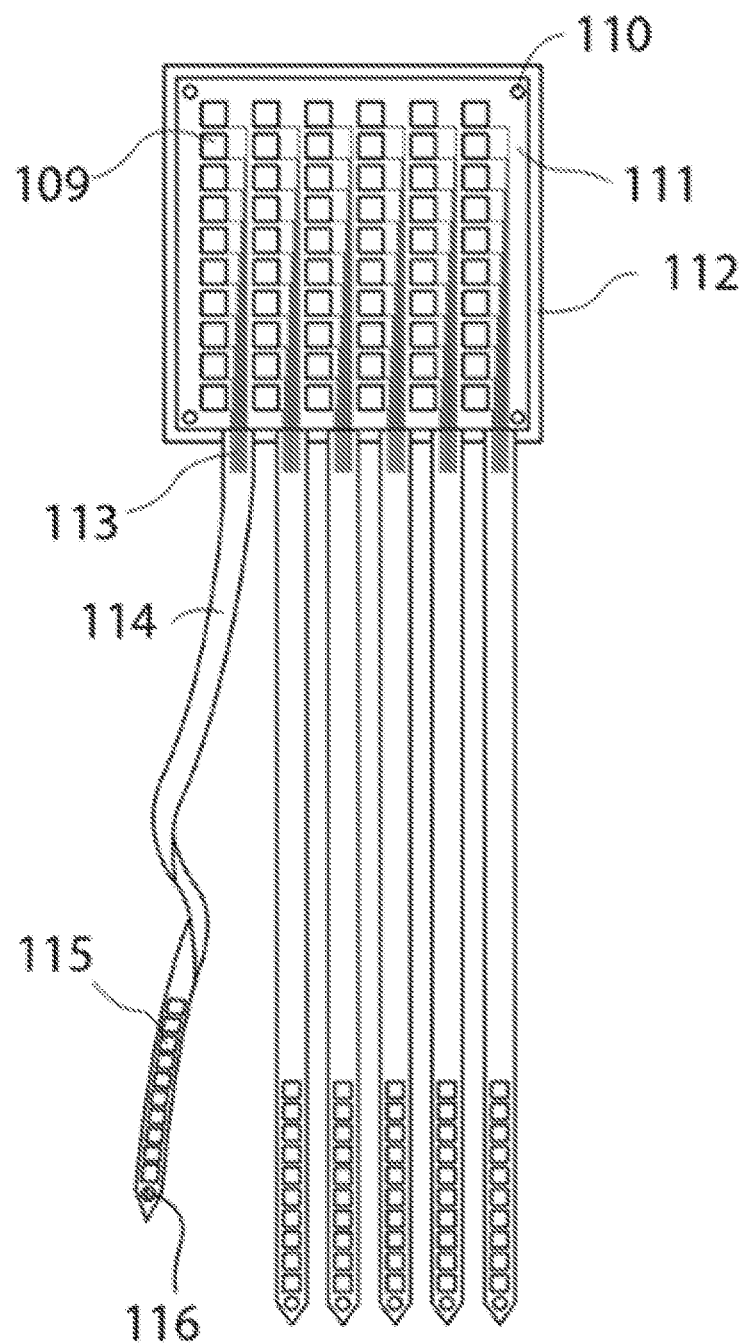
FIG. 1B illustrates a top view of an example ORS-based implantable electronic device implemented based on some embodiments of the disclosed technology.

FIG. 1A illustrates an example optical relay station (ORS)-based implantable electronic device implemented based on some embodiments of the disclosed technology. FIG. 1B illustrates a top view of an example ORS-based implantable electronic device implemented based on some embodiments of the disclosed technology.

An optical relay station (ORS) implemented based on some embodiments of the disclosed technology includes a plurality of optical or opto-electronic elements and flexible electrodes emanating from the ORS. In some implementations, the ORS includes, among others, a plurality of opto-electronic elements 101, 109, a bottom encapsulation layer 103, 112 and a top encapsulation layer 102, 111.

The encapsulation layers 102 and 103 are designed for protecting, sealing and insulating the optical and electrical components and for interfacing with various tissues without adversely impacting the tissues, especially when implanting to a person's brain. Examples of the encapsulation layers 102 and 103 may include Polyimide, SU8, SiO2, Alumina, and Parylene-C.

In some implementations, two or more flexible electrodes emanating from the ORS can be grouped into a plurality of flexible electrode ribbons such that the flexible electrodes in each flexible electrode ribbon are coupled to the optical or opto-electronic elements arranged in a column of an array of the optical or opto-electronic elements in the ORS. In an implementation, the optical or opto-electronic elements arranged in a column of the array and the flexible electrodes in the corresponding flexible electrode ribbon are mapped in one-to-one correspondence. In another implementation, two or more optical or opto-electronic elements can be mapped to one flexible electrode. In yet another implementation, two or more flexible electrodes can be mapped to one optical or opto-electronic element.

In some implementations, the plurality of flexible electrode ribbons can be inserted or implanted into biological tissue at different locations, respectively, that are remote from the plurality of optical or opto-electronic elements. Each flexible electrode ribbon includes a plurality of flexible electrodes coupled to a sub-array (e.g., column) of the array of the optical or opto-electronic elements such that electrical and/or optical signal patterns generated by each sub-array of the optical or opto-electronic elements can represent the biological process in the biological tissue being monitored by the active electrode areas of the corresponding flexible electrode ribbon. The ORS-based implantable electronic device implemented based on some embodiments of the disclosed technology has an advantage in simultaneously monitoring different locations in the biological tissue by grouping the flexible electrodes and the corresponding active electrode areas into different flexible electrode ribbons to allow each flexible electrode ribbon to be inserted in a desired location different from other flexible electrode ribbons. Each sub-array of the optical or opto-electronic elements (e.g., each column of the array of optical or opto-electronic elements shown in FIGS. 1A and 1B) can measure biological process from a desired location without interference with other biological processes being monitored from other locations.

In some implementations, the number of optical or opto-electronic elements in each sub-array of the array of optical or opto-electronic elements may vary depending on different applications of the ORS-based implantable electronic device. In some implementations, the ORS-based implantable electronic device includes the same number of optical or opto-electronic elements in each column of the array as the active electrode areas of each flexible electrode ribbon. In some implementations, however, each sub-array of the array of optical or opto-electronic elements can include more (or less) optical or opto-electronic elements than the corresponding active electrode areas. FIG. 1A shows an example where each column of the array of optical or opto-electronic elements includes seven optical or opto-electronic elements and each flexible electrode ribbon includes six active electrode areas, whereas FIG. 1B shows another example where each column of the array of optical or opto-electronic elements includes ten optical or opto-electronic elements and each flexible electrode ribbon includes ten active electrode areas.

In some implementations, the ORS includes a plurality of optical elements 101, 109 electrically connected to flexible input electrodes 105, 114 extending from the array. In one example, the flexible input electrodes 105, 114 may include a conductor 104, 113 and an insulator covering the conductor 104, 113. The flexible input electrodes may have active electrode areas 106, 115 of the optical element to serve to stimulate and/or monitor a biological process.

In some implementations, the ORS also includes openings 107, 116 on the flexible electrodes to facilitate insertion and implanting the flexible electrodes into tissue.

In some implementations, the ORS device may also include openings 108, 110 in the encapsulation materials to allow for etching underneath the ORS during fabrication steps. In one embodiment, such openings would enable xenon-difluoride gas to etch the silicon substrate underneath the ORS. In some implementations, the ORS also includes optoelectronic elements 101 and 109 that are electrically connected to electrode inputs or outputs 106 and 115 via thin metal interconnects 104 and 113 that are encapsulated and attached to the flexible components 105 and 114. The elements 104, 105, and 106 together comprise a flexible electrode that is electrically connected to the optoelectronic components 101. The elements 113, 114, and 115 together comprise a flexible electrode that is electrically connected to the optoelectronic components 109.

Although not shown in FIGS. 1A and 1B, ORS-based implantable electronic devices may further include a global ground electrode coupled to some of input/output terminals of the optical or opto-electronic elements to provide an electrical ground to the optical or opto-electronic elements.

Figure 1C:
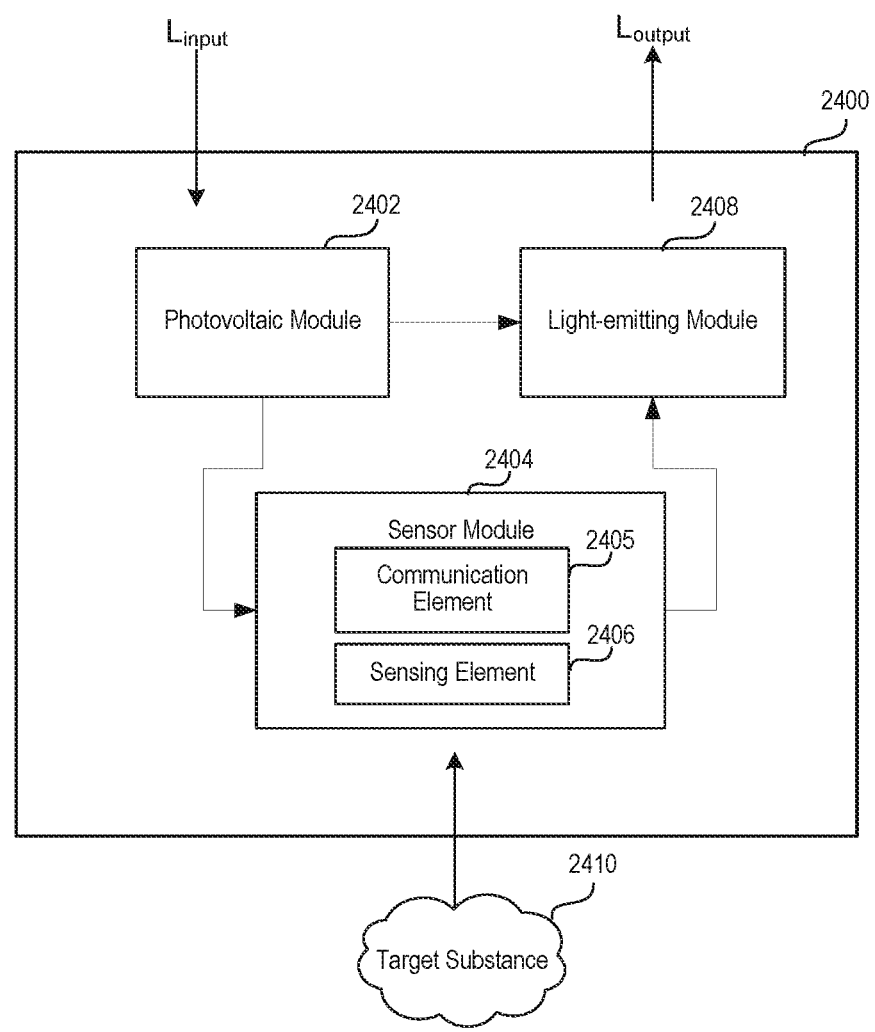
FIG. 1C shows an example of an optical wireless sensor device 2400 that can be implemented to construct the opto-electronic elements 109, 111 shown in FIGS. 1A and 1B.

FIG. 1C shows an example of an optical wireless sensor device 2400 that can be implemented to construct the opto-electronic elements 109, 111 shown in FIGS. 1A and 1B. In this example, the optical wireless sensor device 2400 includes a photovoltaic module 2402 structured to convert incident electromagnetic radiation ($L_{input}$) into electricity. The optical wireless sensor device 2400 also includes a sensor module 2404 coupled to the photovoltaic module 2402 to receive the electricity generated by the photovoltaic module 2402. The sensor module 2404 includes a sensing element 2406 and a communication element 2405. The sensing element 2406 is coupled to the flexible input electrode 105, 114 in FIGS. 1A and 1B and is responsive to a target substance 2410 to produce a response, and the communication element 2405 is structured to generate, based on the response from the sensing element 2406, an electrical sensor signal indicative of a property of the target substance 2410. The optical wireless sensor device 2400 also includes a light-emitting module 2408 coupled to the photovoltaic module 2402 to receive the electricity and coupled to the communication element 2305 of the sensor module 2404 to receive the electrical sensor signal and convert the electrical sensor signal to output electromagnetic radiation ($L_{outout}$) indicative of the property of the target substance 2410. The electricity generated by the photovoltaic module 2402 is used to supply power to the sensor module 2404 and the light-emitting module 2408. In an embodiment of the disclosed technology, the electricity generated by the photovoltaic module 2402 may also be used to generate electrical control signals for controlling the sensor module 2404 and the light-emitting module 2408. In some implementations, the input light may include two input light beams with one beam being converted into power for operating the sensor module 2404 and the light-emitting module 2408, and a second input light beam is used to provide input information and is converted into information associated with operations of the sensor module 2404 and/or the light-emitting module 2408 such as instructions for controlling the sensor module 2404 and/or the light-emitting module 2408. Such two input beams may be at different optical wavelengths for separating them and for processing them separately. Various features for the example in FIG. 1C and other examples in this patent document are disclosed in Cornell's PCT Patent Application No. PCT/US2019/17377 entitled "WIRELESS, OPTICALLY-POWERED OPTOELECTRONIC SENSORS AND DEVICES" and filed on Feb. 8, 2019 which was published under PCT Publication No. WO/2019/157397 on Aug. 15, 2019. The entire disclosure of the PCT Publication No. WO/2019/157397 is incorporated by reference as part of the disclosure of this patent document.

Figure 2A:
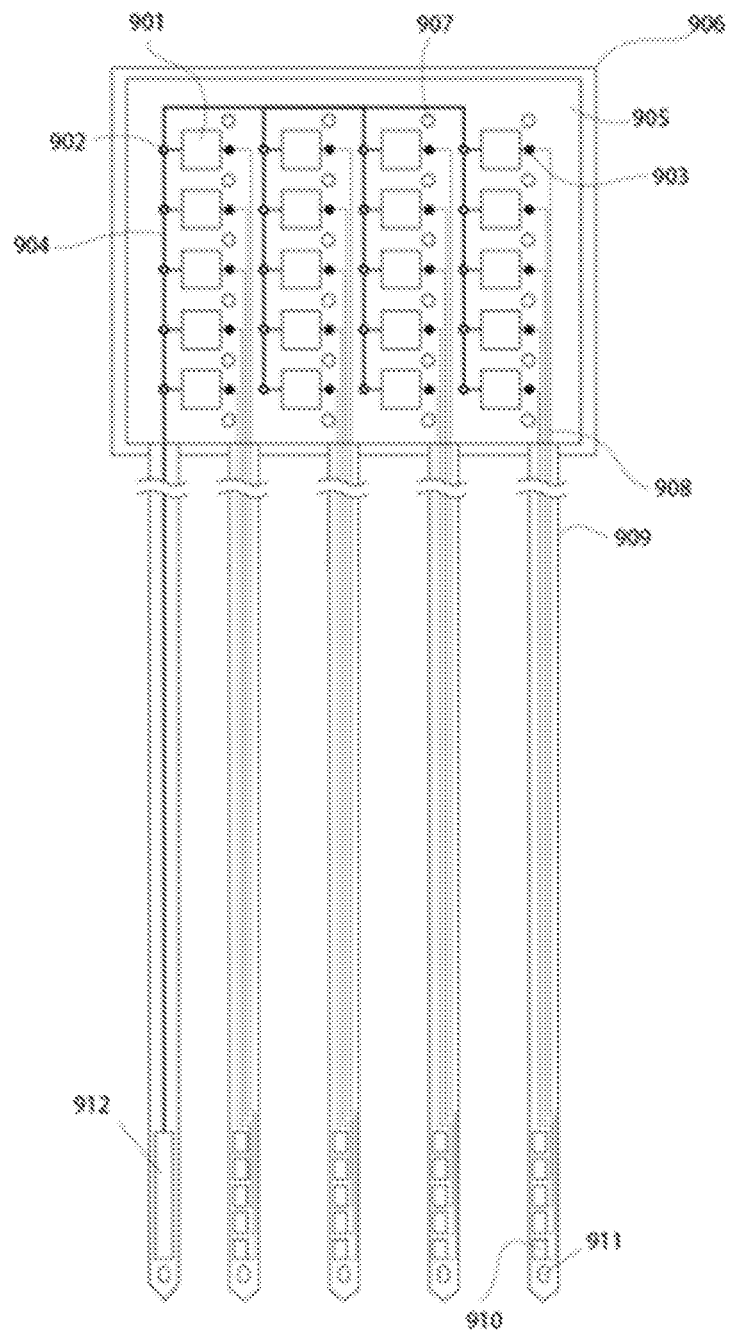
FIG. 2A illustrates a more detailed ORS-based implantable electronic device implemented based on some embodiments of the disclosed technology.

FIG. 2A illustrates an example showing some details of an ORS-based implantable electronic device implemented based on some embodiments of the disclosed technology. In some implementations, the ORS device may include conductive interconnects 908 extending from input/output terminals (902, 903) of the optical elements 901 in the ORS. The interconnects 908 extend to form flexible electrodes (flexible electrode ribbon including a plurality of flexible electrodes) 909 and are covered by an insulating material. In some implementations, the ORS device further includes a bottom encapsulation layer 906 and a top encapsulation layer 905. In some implementations, some of the input/output terminals (902, 903) of the optical elements 901 are electrically connected to a global ground electrode 912, and the others of the input/output terminals (902, 903) of the optical elements 901 are electrically connected to an active electrode area 910. Regularly spaced openings 907 in the bottom encapsulation layer may be formed to allow access to the underlying silicon substrate during fabrication processes. Furthermore, each of the flexible electrode may have an opening at the end to facilitate insertion and implanting the flexible electrode into tissue.

In the context of this patent document, the words "optical element," "opto-electronic element" and other words that includes the word "optical" or "opto-electronic" are used to indicate such a device that can generate electrical signals responsive to light and/or generate light signals based on electrical signals.

As shown in FIG. 2A, in one example implementations, each column of the array of optical elements 901 includes a plurality of optical elements 901 (e.g., five optical elements) coupled to a plurality of active electrode areas (e.g., five active electrode areas in each electrode ribbon 909). In some implementations, the optical elements 901 arranged in a column of the array and active electrode areas in the corresponding electrode ribbon are mapped in one-to-one correspondence. Each optical element 901 is electrically connected to its corresponding active electrode area via an electrical interconnect 908 extending from the array of optical elements 901 on the ORS.

The ORS-based implantable electronic device implemented based on some embodiments of the disclosed technology is structed to monitor different locations in the biological tissue by grouping the flexible electrodes and the corresponding active electrode areas 911 into different flexible electrode ribbons 909 to allow each flexible electrode ribbon 909 to be inserted in a desired location different from other flexible electrode ribbons. Each column of the array of optical elements 901 coupled to its corresponding flexible electrode ribbon 909, which includes a set of active electrode areas, can measure biological process from a desired location without interference with other biological processes being monitored by other flexible electrode ribbon 909.

Figure 2B:
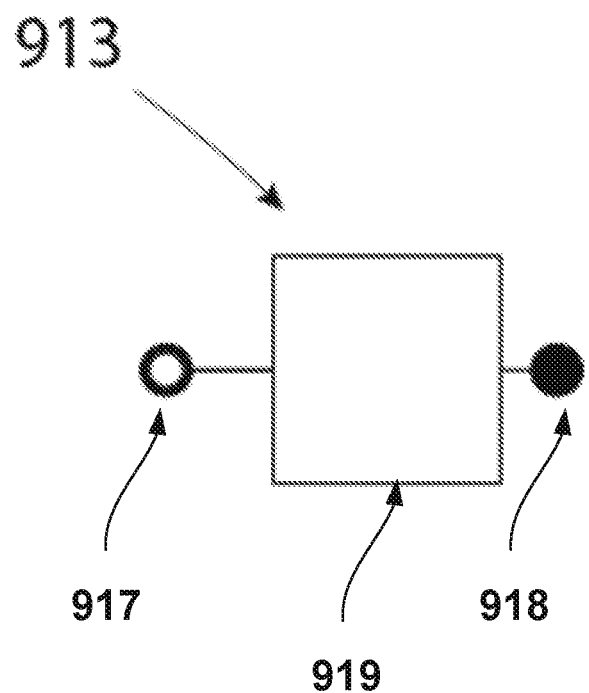
FIG. 2B illustrates the schematic used to denote an example of an optical element applicable to the ORS-based implantable electronic device.

FIG. 2B illustrates the schematic used to denote an example of an optical element 913 applicable to the ORS-based implantable electronic device. The two electrical connects to the optical element 917, 918. The square 919 represents the remaining electrical and optical components composing an optoelectronic device.

Figure 2C:
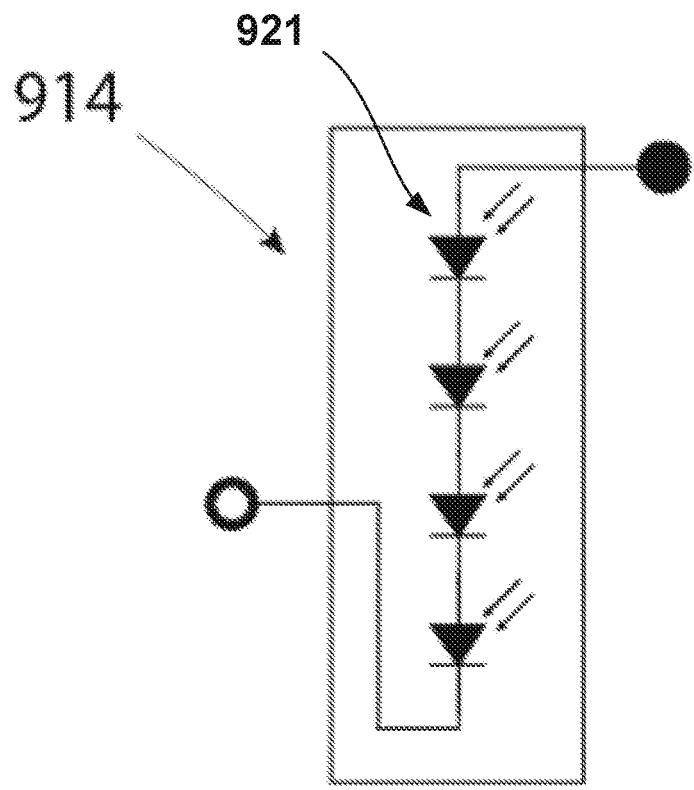
FIG. 2C illustrates a circuit schematic of an example of an optical stimulator applicable to the ORS-based implantable electronic device.

FIG. 2C illustrates a circuit schematic of an example of an optical stimulator 914 applicable to the ORS-based implantable electronic device. In some implementations, the optical element 914 includes multiple silicon photovoltaics 921 (e.g., photodiodes) connected in series. When illuminated, the voltage difference across the two electrical outputs increases.

Figure 2D:
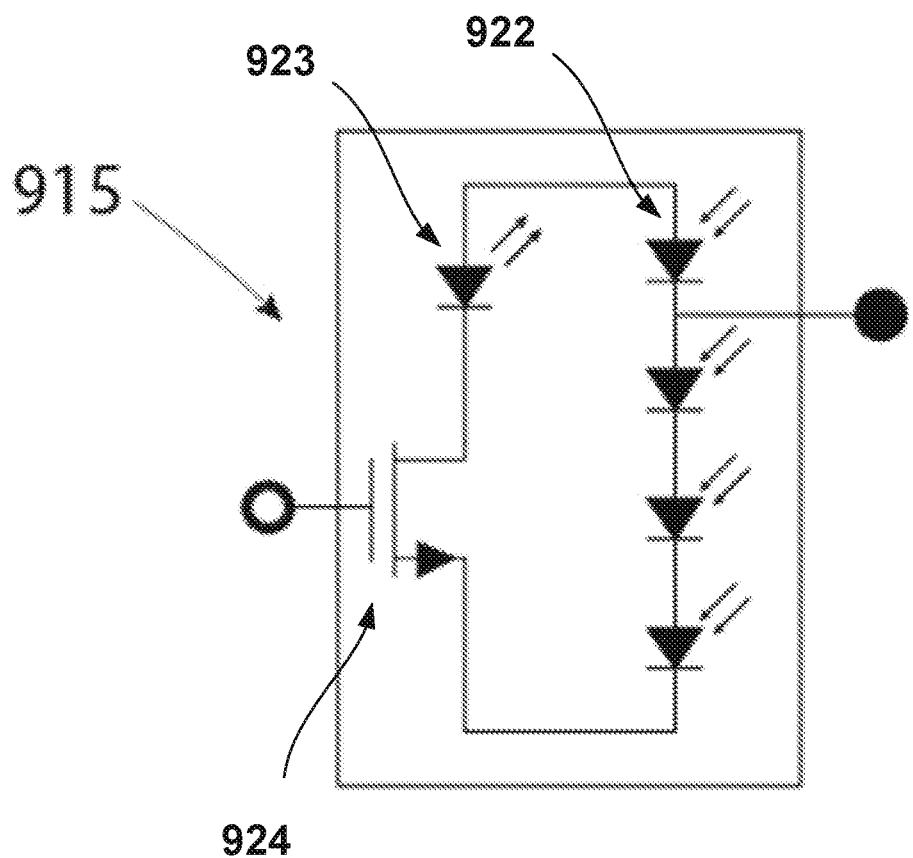
FIG. 2D illustrates a circuit schematic of an example of a single-stage optical voltage amplifier applicable to the ORS-based implantable electronic device.

FIG. 2D illustrates a circuit schematic of an example of a single-stage optical voltage amplifier 915 applicable to the ORS-based implantable electronic device. In some implementations, the first stage of the amplifier may include a resistor (not shown) in series with a switch circuit 924 such as a silicon MOSFET. This stage amplifies the input voltage to the gate of the MOSFET 924. The output of the first stage is connected to the gate of the second stage. The second stage includes a light emitting diode 923 (LED) coupled in series with the MOSFET 924. The photovoltaics 922 coupled in series serve to provide power to the amplifier.

In some implementations, the ORS-based implantable electronic device may include a photovoltaic power supply (as shown as photovoltaic cells 922 coupled in series) coupled to supply power to the LED 923 via a single stage transistor amplifier 924.

Figure 2E:
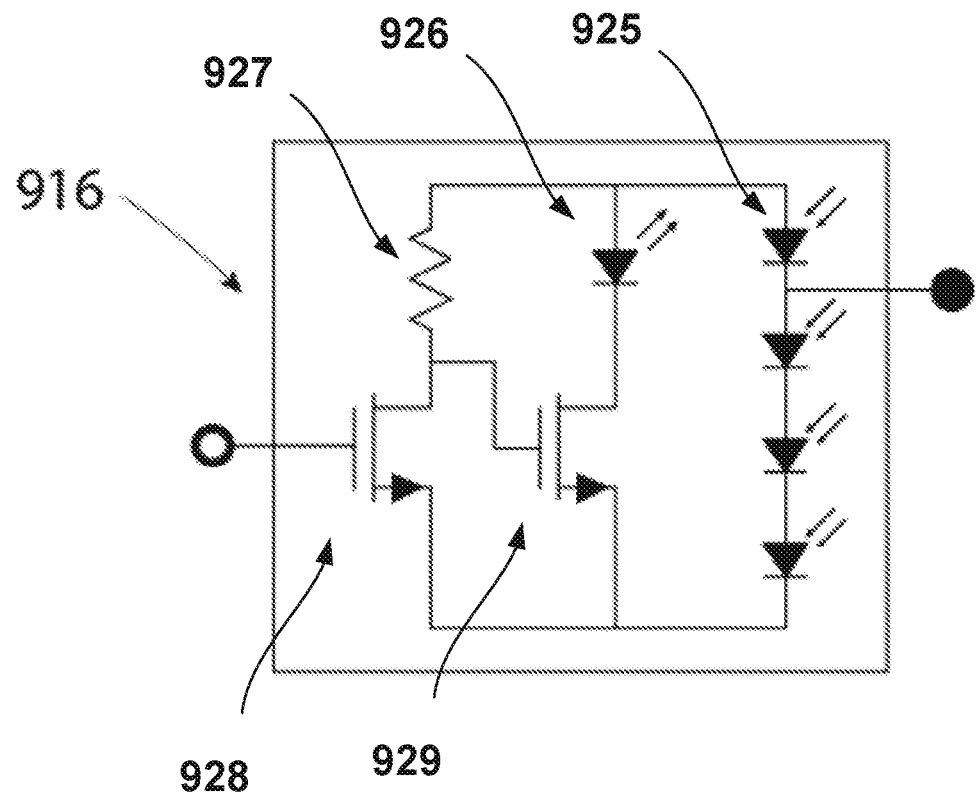
FIG. 2E illustrates a circuit schematic of an example of a two-stage optical voltage amplifier applicable to the ORS-based implantable electronic device.

FIG. 2E illustrates a circuit schematic of an example of a two-stage optical voltage amplifier 916 applicable to the ORS-based implantable electronic device. The first stage of the amplifier includes a resistor 927 coupled in series with a switch circuit 928 such as a silicon MOSFET. This stage amplifies the input voltage to the gate of the MOSFET 928. The output of the first stage is connected to the gate of a switch circuit (e.g., MOSFET) 929 of the second stage. The second stage includes a light emitting device 926 such as an LED coupled in series with the MOSFET 929. The photovoltaics 925 in series serve to provide power to the amplifier.

In some embodiments of the disclosed technology, silicon on insulator (SOI) technology can be used in the fabrication of the ORS-based implantable electronic device. In some implementations, photovoltaics, light emitters, optical voltage amplifier and other electrical and optical elements discussed in this patent document may include an SOI MOSFET, which is a metal-oxide-semiconductor field-effect transistor (MOSFET) device in which a semiconductor layer is formed on an insulator layer which may be a buried oxide (BOX) layer formed in a semiconductor substrate.

As illustrated in FIGS. 2A-2E, an example of a system implemented based on some embodiments of the disclosed technology includes a wireless electronic device that is powered by light, addressed by light, and communicates with light. When one of the optical elements 901 is illuminated by sufficient light, the corresponding active electrode areas 910 of the optical element serve to stimulate and/or monitor a biological process. Since the flexible electrode ribbon 909 and electrical interconnects 908 extend from the ORS, the site being stimulated or monitored can be a remote location that is not spatially fixed relative to the ORS. The array of optical elements forms an optical correspondence to the active electrode elements.

Figure 3:
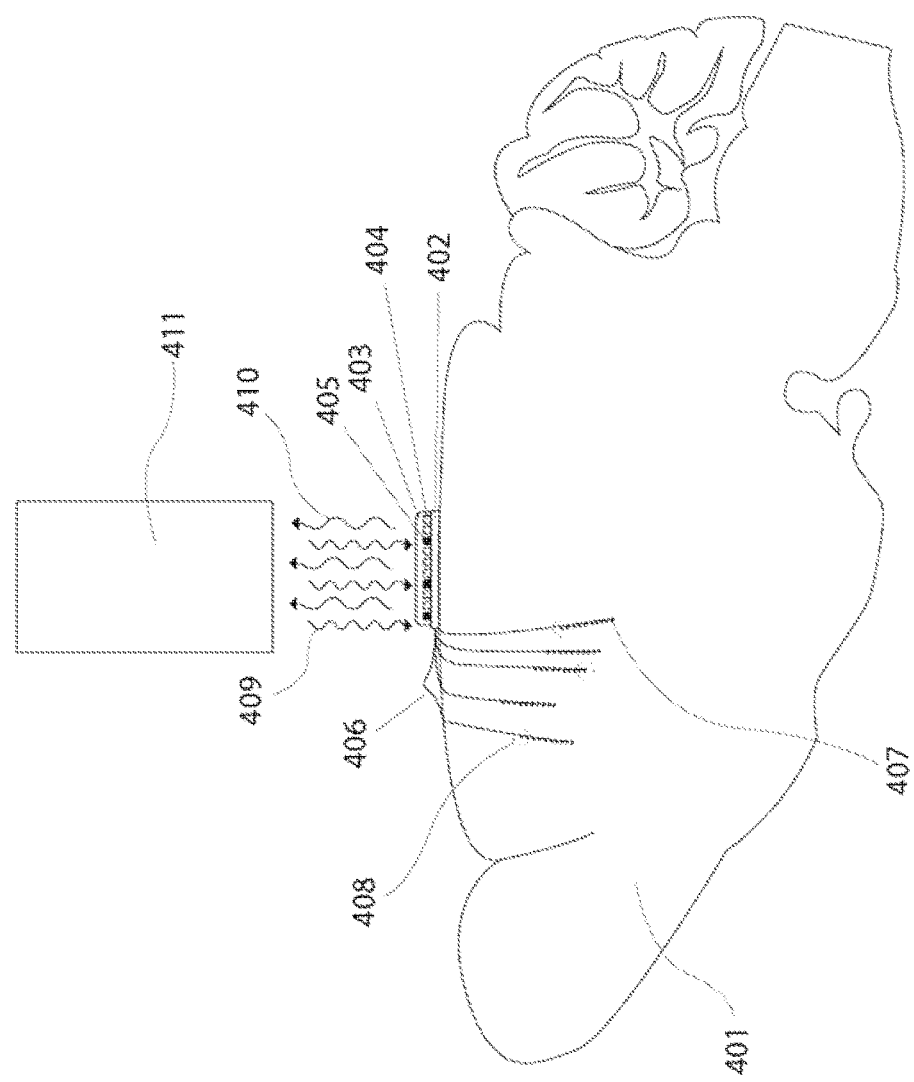
FIG. 3 illustrates the ORS-based implantable electronics being used to monitor and stimulate in a mouse brain.

FIG. 3 illustrates an example of the ORS-based implantable electronics being used to monitor and stimulate in a mouse brain. In some implementations, flexible electrode ribbons 406 of the ORS-based device are implanted into the brain tissue of the brain 401 whereas the ORS is placed on the surface on the brain 401. The optical input and output are delivered and collected with an optical component shown.

In an example mode of operation for ORS-based implantable electronics based on some embodiments of the disclosed technology, the ORS may be placed on the surface of a mouse brain 401. In one example, the ORS may include optical elements 404, 405 and top and bottom encapsulation layers 402, 403. The flexible electrodes 406 extending from the ORS can then be inserted into the tissue of the mouse brain 401. This allows the various active exposed areas of the electrodes 407, 408 to be deep into the tissue while the ORS remains at the surface of the mouse brain 401. Although this embodiment details the application of the ORS-based implantable electronics in the brain, the device could also be used to monitor or stimulate functions in other areas of the nervous system such as muscles and the retina. The ORS can communicate with a remote control and/or monitoring system (e.g., 411).

In some implementations, each flexible electrode ribbon 406 can include a plurality of flexible electrodes and corresponding active electrode areas 407. Each flexible electrode is mapped to an active electrode area so that each flexible electrode ribbon 406 can convey information monitored by a set of active electrode areas to the corresponding sub-array of the optical elements 404, 405. Each sub-array of the optical elements 404, 405 on the ORS-based implantable electronics receives, from its corresponding flexible electrode ribbon 406, electrical signals that represent the biological process monitored by the corresponding set of active electrode areas and convert and/or modulate the information into optical signals to transmit the monitored information to a remote monitoring system 411.

The ORS-based implantable electronic device implemented based on some embodiments of the disclosed technology includes a plurality of flexible electrode ribbons 406 that can be inserted or implanted to monitor different locations in the biological tissue. Information collected by active electrode areas 407, 408 of each flexible electrode ribbon 406 can be represented by an optical signal pattern generated by each sub-array of the optical elements 404, 405. In this way, biological processes occurring in different locations can be simultaneously monitored without interference between different flexible electrode ribbons.

In some implementations, the ORS may include photovoltaics structured to convert input light into electricity, sensors engaged to the active exposed areas of the electrodes 407, 408 and responsive to a target substance to produce an electrical sensor signal indicative of a property of the target substance, and light emitters structured to produce output light that is modulated to carry the electrical sensor signal to wirelessly and optically transmit the electrical sensor signal to the remote control and/or monitoring system. Here, the sensors and light emitters can receive power from the electricity generated by the photovoltaics.

In some example embodiments, the device is configured to allow for high-channel count electrical stimulation. In these embodiments, each optical element in the ORS includes a set of silicon photovoltaics connected in series as illustrated in FIG. 2C. When the silicon photovoltaics associated with a particular active electrode area 910 is illuminated with sufficient light, an electrical pulse is generated and conducted through an interconnect to the active electrode area 910. Here, the circuit can be completed with a global ground electrode 912, allowing current to flow. The system can be further adapted to include a reference and counter electrode. In the example shown in FIG. 3, by illuminating the ORS with a specific spatial pattern of light 409, one or more photovoltaics that are illuminated by the light 409 can generate one or more corresponding electrical pulses. In the illustrative example of FIG. 3, the photovoltaic 405 that is illuminated by light generates an electrical pulse in response to the specific spatial pattern of light 409, and the photovoltaic 404 that is not illuminated by light does not generate an electrical pulse. This patterned light results in electrical pulses in a specified configuration in the tissue. Hence, by projecting an optical image onto the ORS, one effectively produces a corresponding electrical pattern in the tissue.

Sensors may be used to monitor biological functions in real-time. In some example embodiments configured for neural recording, each optical element of the ORS is a single-stage or two-stage optical voltage amplifier as shown in FIG. 2D and FIG. 2E. Such optical voltage amplifiers may include photovoltaics coupled in series with a light-emitting diode (LED) and a MOSFET and may be capable of resolving electrical impulses from cell activity. When illuminated, changes in the voltage at the input electrodes result in modulation of the current through the circuit, which changes the amount of light output by the LED. In this way, each optical element allows for the monitoring of voltage changes using an optical source. In such an embodiment of the ORS-based implantable electronics, the output light pattern 410 is a representation of the voltage at corresponding active electrode sites such as 407. Hence, by illuminating the ORS and monitoring the ORS with a high-speed detector or camera with image sensor such as charged-coupled device (CCD) camera, a large number of active electrodes in the brain can be optically monitored.

Figure 4:
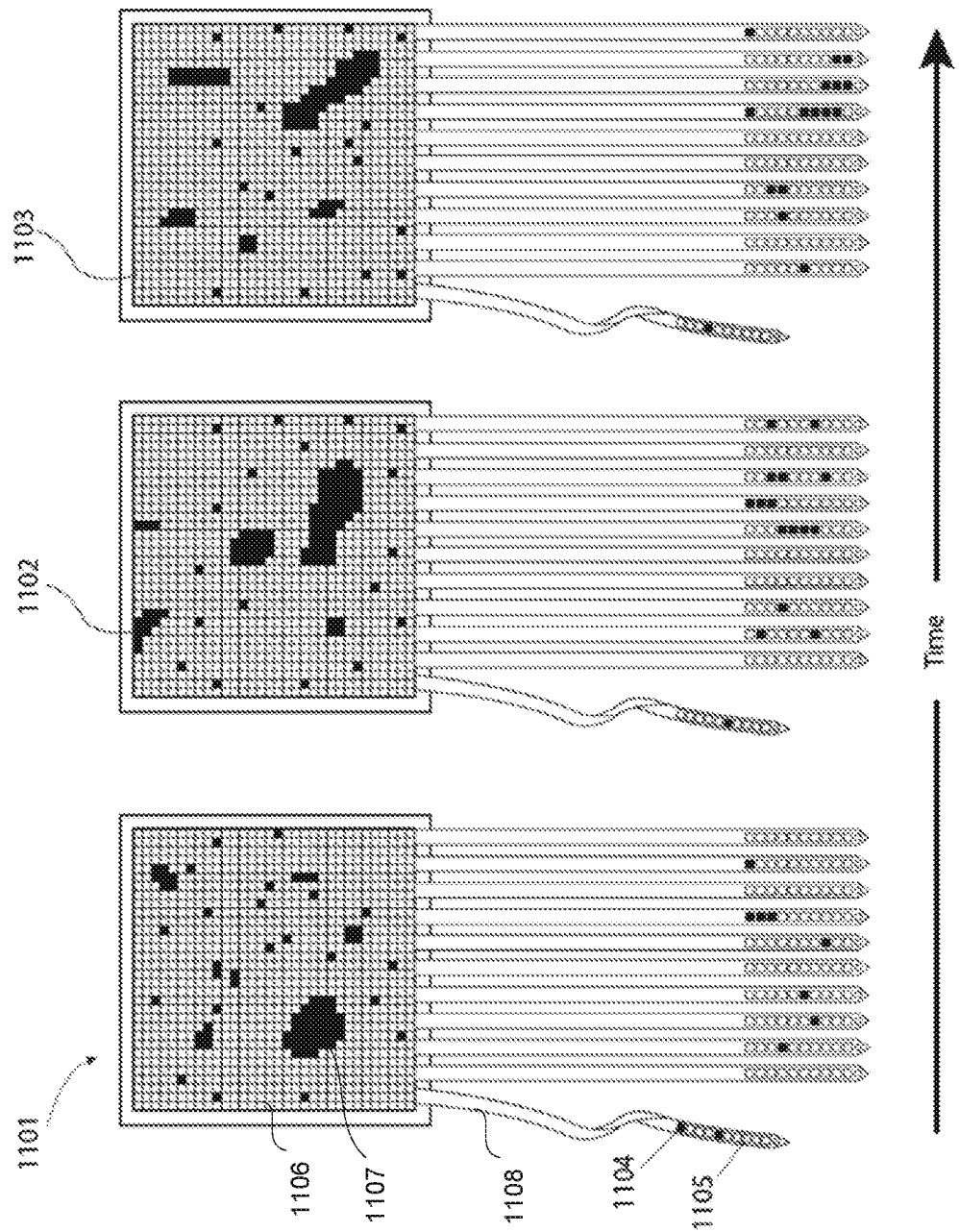
FIG. 4 illustrates an ORS-based device being used to optically monitor voltage changes at the active electrode areas.

FIG. 4 illustrates an ORS-based device being used to optically monitor voltage changes at the active electrode areas. The three illustrations 1101, 1102, 1103 depict a changing optical signal over time. Here, each of the output light patterns 1101, 1102, 1103 is a representation of the voltages at corresponding active electrode sites 1104, 1105. Optical elements that are indicating neural activity are shown filled with black. Optical elements that are not indicating neural activity are shown without fill. As shown in FIG. 4, a recording device implemented based on some embodiments of the disclosed technology can monitor many sites (e.g., 1024 sites) simultaneously.

In some implementations, the ORS-based device includes an array of optical elements 1106, 1107 and a plurality of flexible electrode ribbons 1108 coupled to the array of optical elements 1106, 1107. Each flexible electrode ribbon 1108 can include a plurality of active electrode areas 1104, 1105 that is mapped to the array of optical elements 1106, 1107 so that information measured by the plurality of active electrode areas 1104, 1105 can be represented as patterns of activated/deactivated optical elements 1106, 1107 as shown in FIG. 4.

In some embodiments of the disclosed technology, features of the disclosed ORS-based implantable electronics may include the followings:

First, an input pattern of light can be used to wirelessly create a corresponding pattern of electrical stimulation. Second, an output pattern of light can be used to wirelessly monitor biological processes. Third, a plurality of optical elements used to relay input or output electrical signals from electrodes are deeper into tissue than the ORS. Fourth, the spatial configuration of the flexible electrodes is not fixed in one configuration with respect to the ORS.

The device implemented based on some embodiments of the disclosed technology may have advantages over a sensor or stimulator that is electrical without being optical in any aspect. First, some embodiments of the disclosed technology can be applied to a high-channel count stimulation device with a very large number of stimulation sites (e.g., over 10,000 sites). In one example, a high-channel count stimulation device can be implemented using an implantable device with 10,000 electrically isolated wires egressing and connected directly to the device. However, the devices would be produced and then serially wire-bonded the 10,000 connections to the devices and a bulky bundle of wires would egress out of the subject using the device. These issues make such an option both expensive to implement and too bulky to be broadly useful. In another example, high-channel count stimulation device can be implemented using on-board multiplexing that allows for fewer than 10,000 wires egressing and connected directly to the device. This is a scalable approach but requires sophisticated multiplexing circuitry built into each device. For typical recording speeds, this would require multiplexing circuitry capable of recording and reporting out 10,000 channels being readout at greater than 10 kHz bandwidth. Each device would be cost prohibitive to be feasible for large-scale use.

In some embodiments of the disclosed technology, a high-channel count stimulation device with a very large number of stimulation sites can be implemented using optical devices such as a digital micromirror, a spatial light modulator, and/or a liquid crystal display for illuminating an array of stimulators or sensors. By converting the input and output signals into a 2D array of light, the device based on some embodiments of the disclosed technology can use such optical devices. For example, a 1024 by 768 digital micromirror array can be used to multiplex greater than 786,000 channels. Also, a high-speed CCD camera with greater than 1 kHz bandwidth can be used to record output patterns of light with high-channel counts. The ORS can turn the input and output electrical signals into a 2D optical signal that can be read or output. By converting the signal to a wireless light signal, the multiplexing functions can be external. In this way, the implantable device based on some embodiments of the disclosed technology can be made less expensively.

Figure 5:
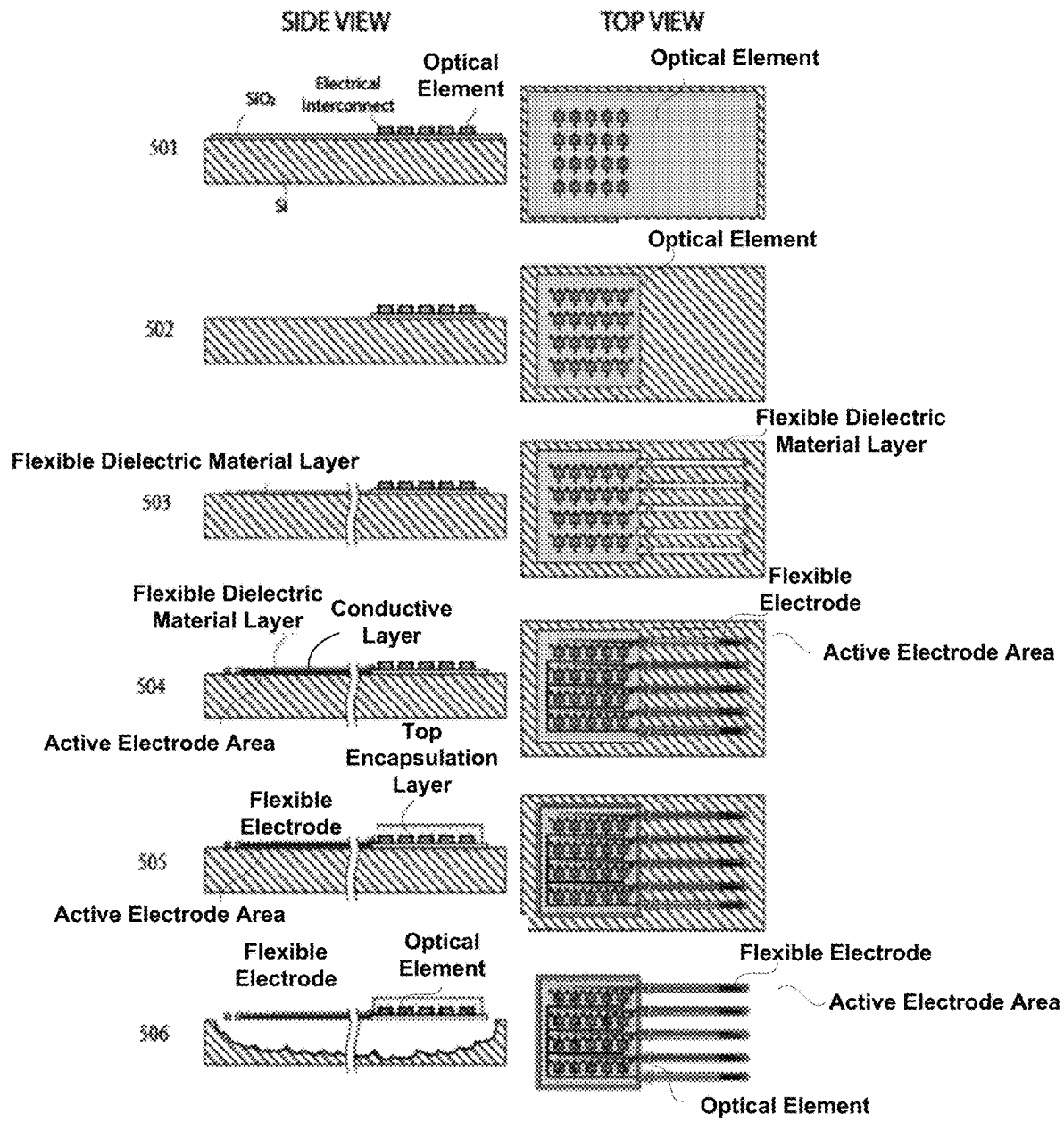
FIG. 5 illustrates an example fabrication method of an ORS-based implantable electronic device based on some embodiments of the disclosed technology.

FIG. 5 illustrates example fabrication processes 501-506 of the ORS-based implantable electronic device based on some embodiments of the disclosed technology. This process flow includes the fabrication of optical elements on a silicon-on-insulator (SOI) substrate, the patterning of a buried oxide (BOX) layer as a bottom encapsulation, patterning of the flexible electrode, patterning of the top encapsulation layer of the ORS-based device, and the selective etching of the substrate releasing the ORS-based device. The fabrication process of the ORS-based implantable electronic device based on some embodiments of the disclosed technology may include forming one or more SOI MOSFETs on the ORS-based implantable electronic device.

Figure 6B:
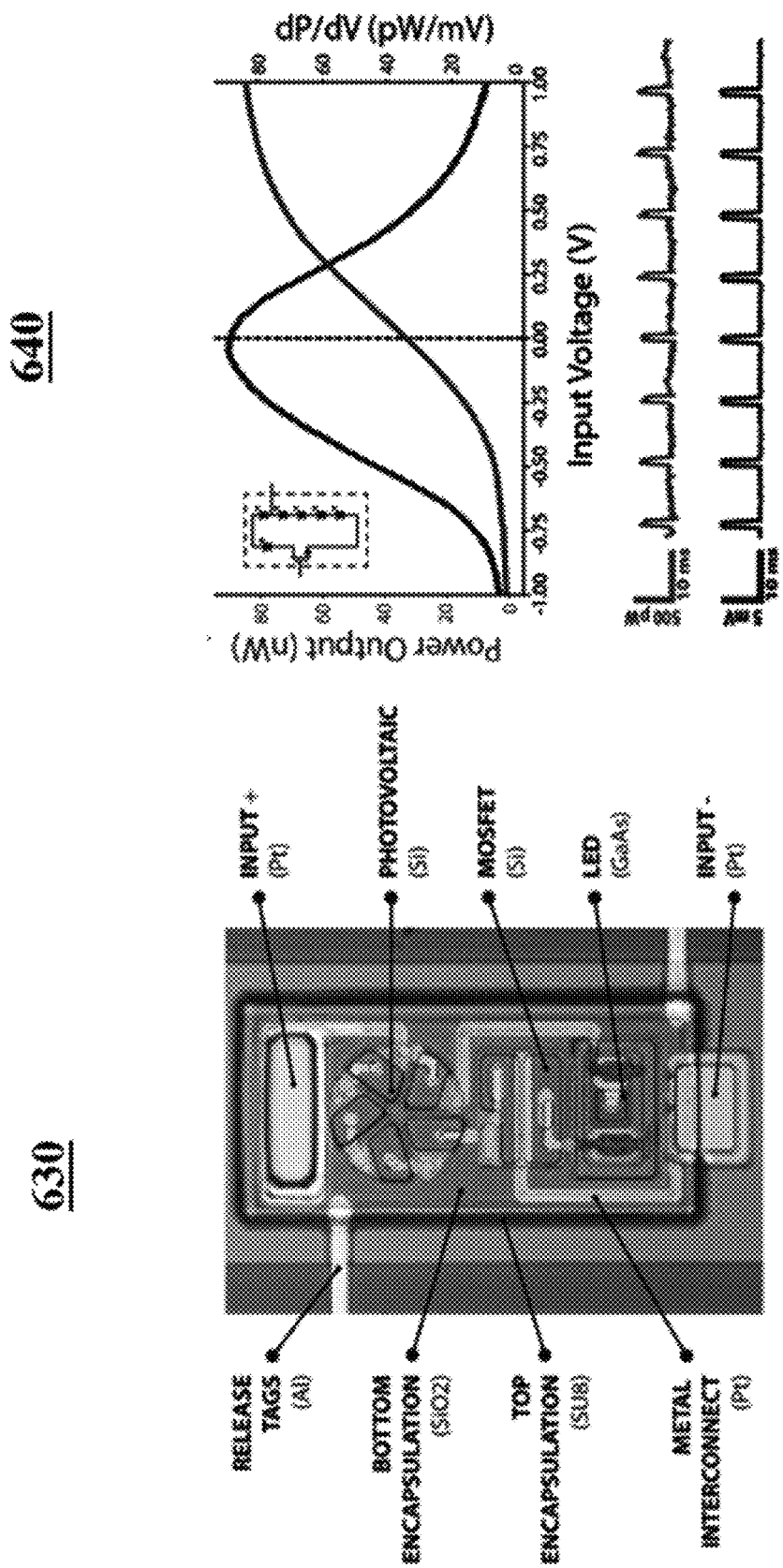
FIG. 6B shows an optical voltage amplifier fabricated on an SOI substrate and the corresponding optical output characteristics. Components of the optical element are labeled.

FIG. 6A shows an optical voltage amplifier fabricated on an SOI substrate and the corresponding current-voltage characteristics under illumination. Responses for 4, 5, and 6 microscale photovoltaics connected in series are shown. FIG. 6B shows an optical voltage amplifier fabricated on an SOI substrate and the corresponding optical output characteristics.

Referring to FIG. 5, at 501, a plurality of optical devices is produced on an SOI substrate. The optical devices may be formed using of planar photolithography without need for wire-bonding or other bulky interconnect methods. These optical devices can include, but are not limited to, optical stimulators including silicon photovoltaic devices for stimulation and electrical to optical voltage amplifier (also referred to as a voltage to optical transducer) for recording. An example of photovoltaics produced on an SOI substrate for stimulation is shown in FIG. 6A at 610, and corresponding performance characteristics at 620. An example of an optical voltage amplifier is shown at FIG. 6B at 630 with a corresponding performance characteristic shown at 640. In both embodiments, each optical element has two electrical interconnects used for input and output. The schematic representations of examples of the optical element are also shown in FIGS. 2B, 2C, 2D, and 2E.

In some example embodiments, each optical element occupies an area less than 1 mm$^2$ on the ORS. The optical stimulators shown in FIG. 6A occupy an area of approximately $(50\,\mu m)^2$. Accordingly, provided an ORS occupies an area of $(5\,mm)^2$, 10,000 individual optical stimulators can fit onto a single device. For the optical voltage amplifiers shown, over 2,000 optical stimulators can fit on an ORS with area $(5\,mm)^2$.

As shown in FIG. 5 at 502, following the formation of optical elements, the buried oxide layer (BOX) that includes silicon dioxide ($SiO_2$) of the SOI substrate can be patterned. The buried oxide layer can be patterned via photolithography and wet chemical etching with hydrofluoric acid or dry reactive ion etching (RIE) in $CHF_3/O_2$ chemistries. The remaining $SiO_2$ layer serves as the bottom encapsulation layer of the ORS as shown in FIG. 2A at 906. Regularly spaced openings in the bottom encapsulation layer at 907 may be made to allow access to the underlying silicon substrate in subsequent steps.

As shown in FIG. 5 at 503, a flexible dielectric material layer for forming the flexible electrode is disposed in the vicinity of the optical elements. In some implementations, the substrate SUB for forming the flexible electrode may include a flexible dielectric material layer, which becomes the bottom layer of the flexible electrode as will be discussed below. the flexible dielectric material layer can be patterned using lithography techniques. In some example embodiments, the flexible dielectric material layer (the bottom layer of the flexible electrode) includes a negative tone photoresist SU-8. In other embodiments, this bottom layer includes polyimide. In some implementations, the bottom layer has two features: 1) the layer needs to be thin enough to allow for the electrode to be flexible when released from the surface and 2) be biocompatible for use in tissue. As SU-8 and polyimide can be produced at thickness less than 10 microns and are biocompatible, they meet these criteria. Other materials may be used instead of SU-8 or polyimide.

As shown in FIG. 5 at 504, conductive layers (e.g., metal interconnects) and top insulating layers of the flexible electrodes can be deposited and patterned. Metals and conductive films used can include, but are not limited to, Pt, TiN, Au, and PEDOT:PSS. In some example embodiments, the metal can be deposited by metal sputter deposition. The metal interconnects connect to an optical element connection at 903 in FIG. 2B and extend as shown in FIG. 2A at 908 to flexible electrode ribbon 909 emanating from the ORS to an active electrode area 910. In some example embodiments, the other connection of the optical element is connected to a global ground 912 providing a global reference for the electrical potential of the optical elements. The top layer of the flexible electrode can be configured with any sufficiently thin biocompatible polymer or dielectric. In some implementations, the top layer of the flexible electrode can include, but is not limited to, SU-8, polyimide, SiO2, and silicon nitride. The top insulating layer of the flexible electrode may be patterned to isolate the electrical interconnects from one another and the surrounding tissue, except at the active electrode areas shown at 910. Furthermore, the top and bottom insulator layers of the flexible electrode are patterned to have an opening at the end shown at 911 in FIG. 2A. This will facilitate insertion and implanting the flexible electrode into tissue as detailed below.

As shown in FIG. 5 at 505, a top encapsulation layer of the ORS is deposited and patterned. In some example embodiments, the top encapsulation layer can also include SU-8. The top encapsulation layer serves to electrically isolate the optical elements and electrical interconnects. The top encapsulation layer is also patterned with openings corresponding to the bottom encapsulation layer openings shown in FIG. 2A at 907. This also serves to allow access to the underlying silicon substrate in subsequent steps.

In cases where minimally invasive electrodes are desired, the minimal cross-section of the flexible portion of the disclosed ORS-based implantable electronics can be kept to dimensions less than $(50\ \mu m)^2$. The top and bottom insulating layers as well as the metal interconnects can be kept to a thickness of less than 1 micron each, the smallest dimension of the flexible electrode can be kept under 10 microns. This can reduce glial scaring and other damage associated with larger implantable electrodes or electronics.

As shown in FIG. 5 at 505, after the patterning and production of the ORS and flexible electrodes, the device can be removed from the underlying substrate by selective etching of the silicon substrate with xenon-difluoride ($XeF_2$) vapor etching, or other technique. The materials in some embodiments of the device may be chosen to be negligibly etched by the $XeF_2$ release process.

Figure 7:
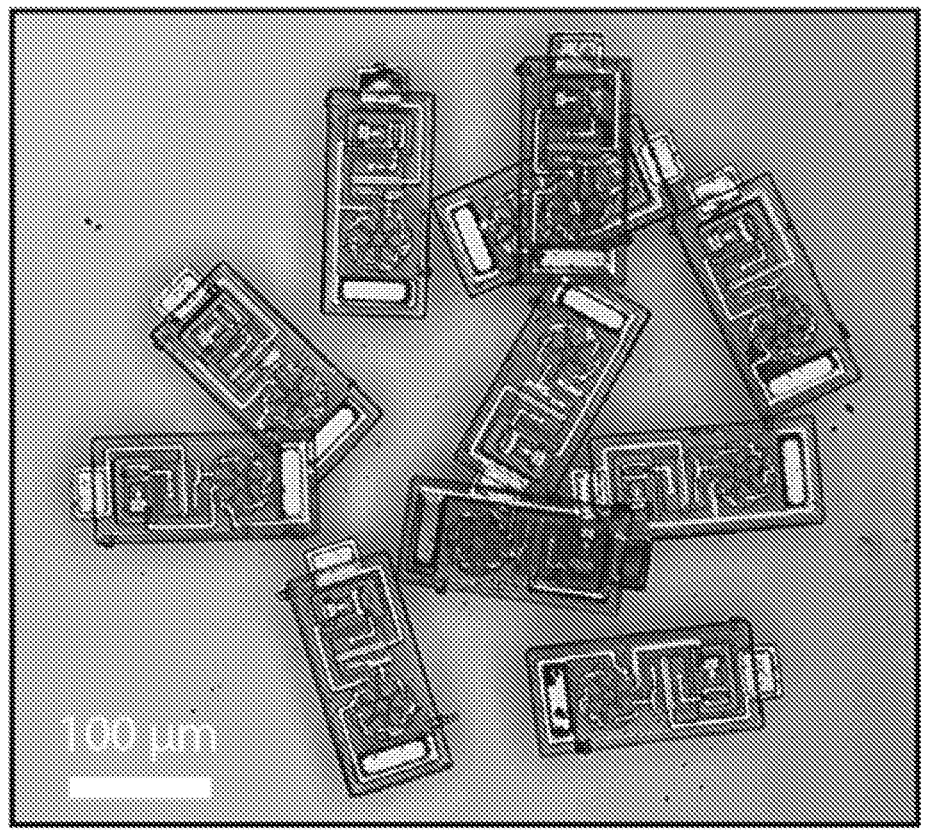
FIG. 7 shows a set of optical voltage amplifiers released from the SOI substrate using methods based on some embodiments of the disclosed technology.

FIG. 7 shows a set of optical voltage amplifiers released from the SOI substrate using methods based on some embodiments of the disclosed technology. An example of encapsulated optical voltage amplifiers with exposed active electrodes released from the substrate using the foregoing methods shows that the $XeF_2$ is selective enough to enable the release of such devices with negligible etching of the exposed materials. Furthermore, to allow for undercutting of the ORS, openings can be made in both the top and bottom encapsulation layer. This allows for the ORS to be patterned at larger scales than would otherwise be feasible due to the time required for $XeF_2$ undercutting.

Figure 8:
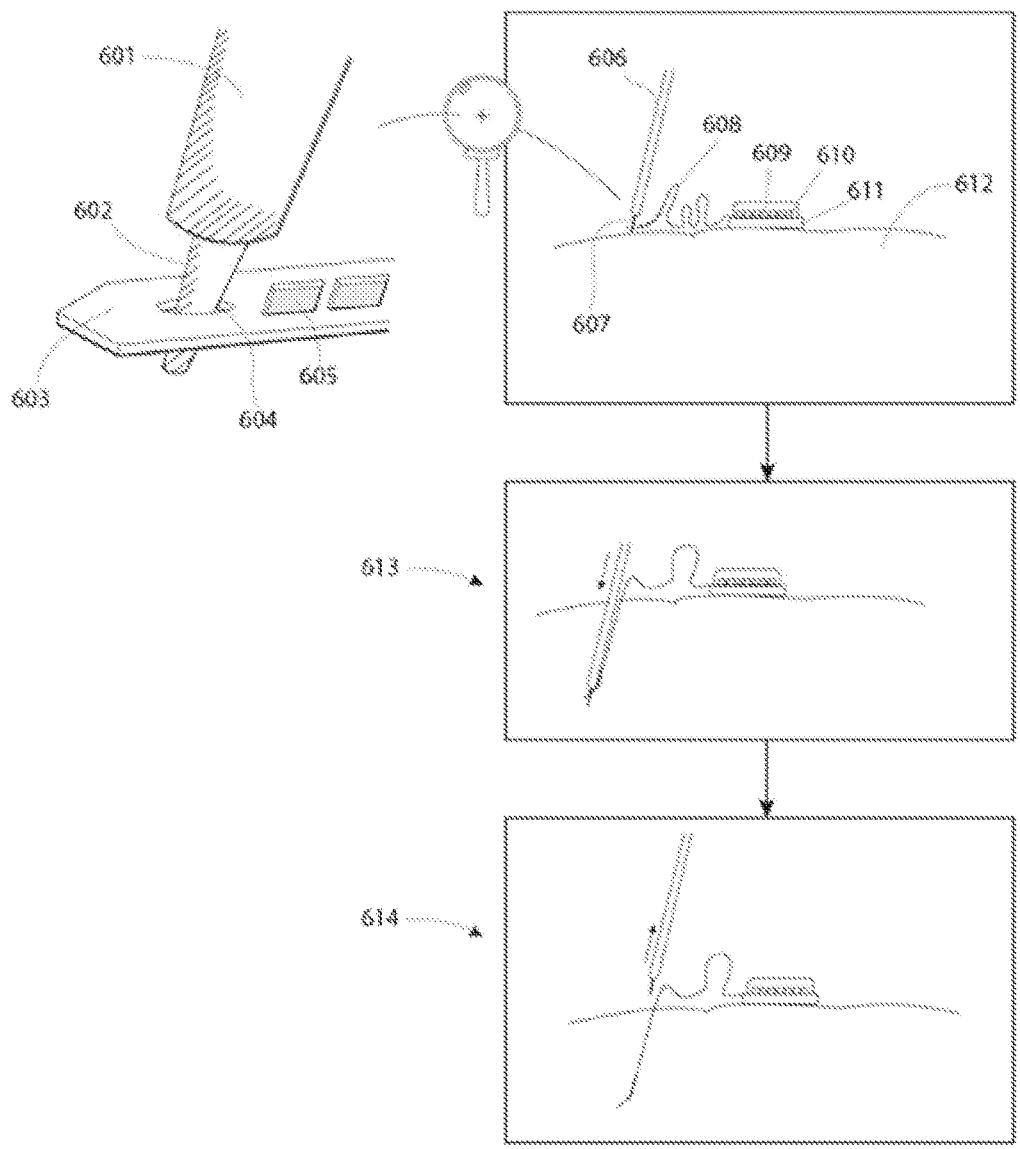
FIG. 8 illustrates an example method of implantation of the flexible electrode portion of the ORS-based device based on some embodiments of the disclosed technology.

FIG. 8 illustrates an example method of implantation of the flexible electrode portion of the ORS-based device based on some embodiments of the disclosed technology. In some implementations, a rigid probe with protrusion is used to engage the flexible electrode when pushing into tissue and then disengage from the flexible electrode when removed. This leaves behind the flexible electrode, embedded in tissue.

In some example embodiments, implantable electronics are implanted to monitor and stimulate regions of the brain. To monitor neural activity and deep-brain stimulation, a region of the brain is exposed by removing the skull and, depending on the circumstances, removing the dura surrounding the brain. The implantable electronics based on some embodiments of the disclosed technology may have the ORS placed on the surface of the brain on or under the dura with the flexible electrodes implanted into the tissue at desired locations. In some example embodiments, the flexible electrodes can be placed on the surface of the brain for monitoring, e.g. electrocorticography (ECoG). In some example embodiments, when the active electrode areas are desired to be in the tissue, a method detailed in FIG. 8 can be used. After the implantable electronics are placed on the surface of the brain, a rigid insertion probe shown at 606 and 601 with a protruding tip shown at 607 and 602 is used to push the flexible electrode 608 into tissue 612. The opening 604 in the top and bottom insulator layers of the flexible electrode 603 is patterned such that only the protruding portion of the probe can pass through. The rigid probe 606 and 601 is chosen to have a small cross-section to minimize damage to the surrounding tissue during insertion. In one embodiment, this rigid probe can be silicon and processed for silicon microneedles. In some example embodiments, the implantable electronics may include photovoltaics 610 disposed between a bottom encapsulation layer 611 and a top encapsulation layer 609.

The probe 606 and 601 is inserted in one direction into the tissue 613 to the desired location. During this insertion, the opening 604 of the flexible electrode 603 is engaged to the probe 606 and 601. When the rigid probe 606 and 601 is removed in the other direction, the flexible electrode 603 is disengaged from the rigid probe 614, leaving the flexible electrode 603 in tissue with the active electrode area 605 at the desired location. This process can be repeated to yield various flexible electrodes (e.g., 603) at various sites in the tissue without the need for a constrained spatial configuration. This adds versatility to the ORS-based implantable electronics in comparison with other rigid prior art used form neural recording and stimulation.

Figure 9:
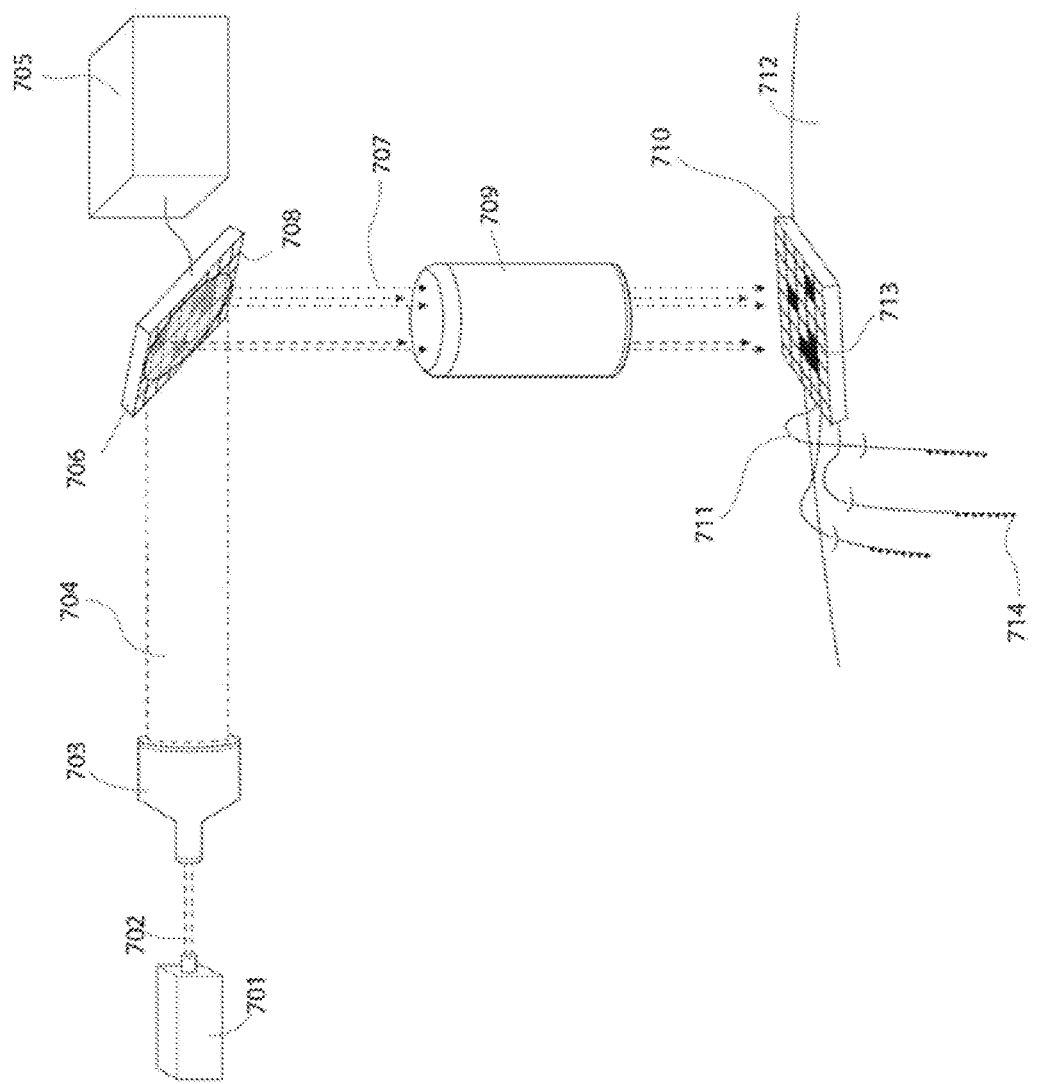
FIG. 9 illustrates an example method of use of the ORS-based implantable electronics for one embodiment where the optical elements and active electrode areas are configured to stimulate regions of tissue.

FIG. 9 illustrates an example method of use of the ORS-based implantable electronics for one embodiment where the optical elements and active electrode areas are configured to stimulate regions of tissue. A spatial light modulator is configured to pattern light that is projected onto the ORS-based device 710.

In some example embodiments, the disclosed implantable electronics may be used for stimulating and monitoring neural activity in tissue. Flexible electrodes 711 of the implantable electronics based on some embodiments of the disclosed technology may be inserted into tissue 712 and the ORS 710 rests on the surface of the tissue. Here, the optical elements of the ORS are such that when illuminated they produce an electrical pulse at the corresponding active electrode area. To address the ORS 710 and cause stimulation at the active electrode areas 714, the following occurs. A laser diode 701 produces an un-patterned beam of light 702. The beam can be shaped to a different size 704 with a beam expander 703. This un-patterned light 702 is then directed onto the surface of an optical spatial modulator such as a digital micromirror display (DMD) 706 to modify the un-patterned light 702 to carry a 2-D spatial pattern. The DMD 706 may include an array of individually addressable micromirrors 708. In various implementations, DMDs can have thousands (or more) individually addressable micromirrors. The micromirrors 708 can be positioned to either direct the light incident on them onto the ORS or away from the ORS. The array of micromirrors can be controlled externally by controller 705 with via digital addressing of the device, either through a computer or other electronic device.

The light reflected off of the DMD 706 towards the ORS 710 can be selectively patterned into a spatial pattern=707. The pattern 707 can be passed on to the ORS directly or through additional optical components 709 such as an endoscope, optical fiber, optical fiber bundle, microscope, or other optical device. For example, the patterned light 707 may include a pattern where certain pixels in the pattern are dark so such dark pixels will not turn on certain optical or opto-electronic elements in in the ORS 710 to generate electrical signals to the electrodes while other pixels in the pattern are on and thus can illuminate corresponding optical or opto-electronic elements in in the ORS 710 to generate input electrical signals to electrodes. For another example, the patterned light 707 may include a pattern of various levels of optical power at different pixels or locations in the pattern to generate electrical input signals to electrodes from the optical or opto-electronic elements in in the ORS 710 so that this optical pattern is transferred into a pattern of different electrical input signals to the electrodes interacting with a target issue, allowing various controllable electrical signals to the electrodes for stimulating the target tissue to produce responsive electrical signals from the tissue. The electrodes are used to transmit the responsive electrical signals from the electrodes back to the optical or opto-electronic elements in in the ORS 710 which produce optical output signals based on the responsive electrical signals as monitored information. Such uses of the patterned incident light result in a corresponding activation of some selected optical devices 713 on the ORS 710 and causing a stimulus at the corresponding active electrode areas 714.

Figure 10:
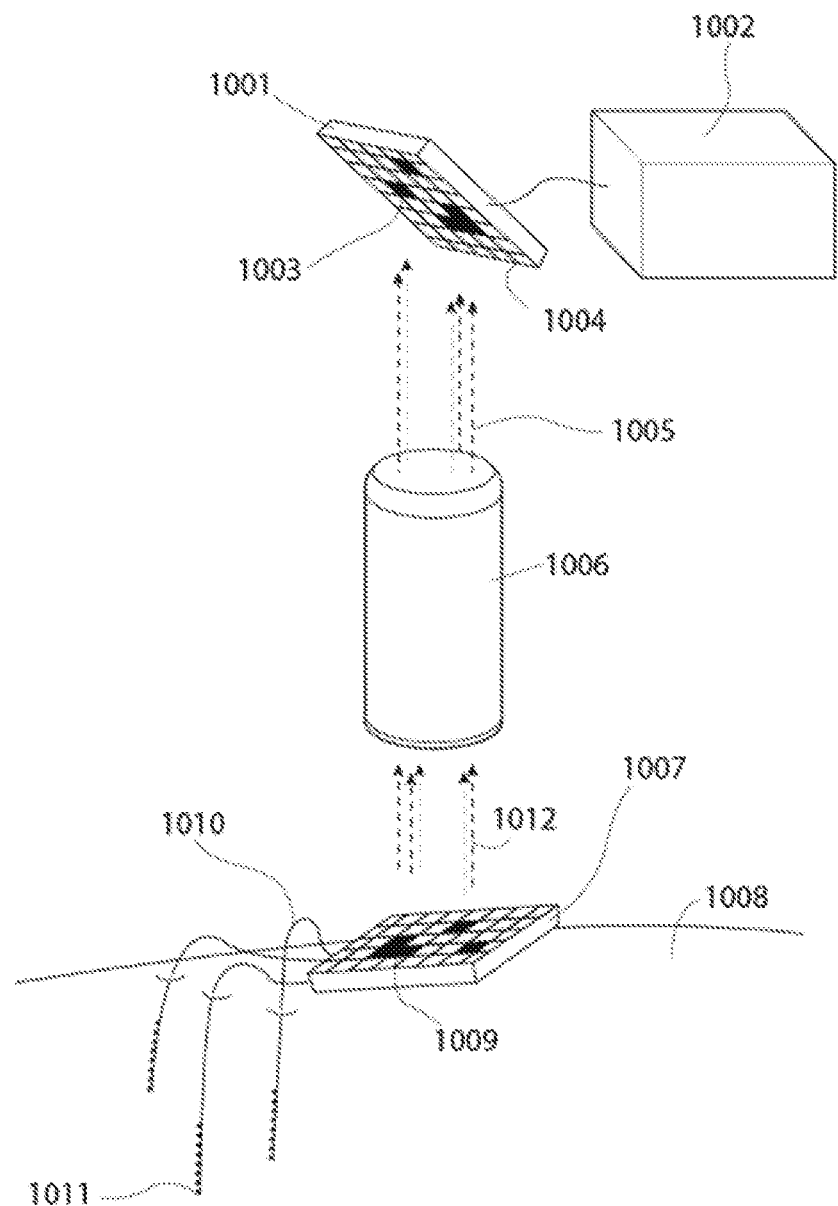
FIG. 10 illustrates an example method of use of the ORS-based implantable electronics for one embodiment where the optical elements and active electrode areas are configured to monitor cellular activity in regions of tissue.

FIG. 10 illustrates an example method of use of the ORS-based implantable electronics for one embodiment where the optical elements and active electrode areas are configured to monitor cellular activity in regions of tissue. In some implementations, an optical element is used to project the output of the ORS 1007 onto a detector.

FIG. 10 depicts an example embodiment for recording neural activity. Here the configuration of the installed ORS-based implantable electronics is the same as described above. However, in this example the optical elements 1009 of the ORS 1007 are optical voltage amplifiers which optically communicate the voltage measured at the active electrode areas 1011 with respect to the global ground. The output light pattern 1012 from the ORS 1007 is a representation of the voltage measured at the corresponding active electrode areas. The light pattern can be collected into an optical element 1006 and projected onto the surface of a light sensing device such as a CMOS or CCD camera 1001. The recording of the image sensing pixels 1003, 1004 (e.g., CMOS or CCD sensing pixels) by an external digital device or computer 1002 provide a recording of the voltages at the active electrode areas in tissue. The ORS 1007 in this instance converts the electrical signals into a two-dimensional, optical representation of the data in a way that can be easily monitored by a detector with sufficient spatial and temporal resolution. Some example embodiments perform both stimulus and recording using a single ORS-based device.

Some applications of the disclosed ORS-based implantable electronics include, but are not limited to, deep-brain stimulation, neural recording, electrocorticography, electrocardiography, electrical muscle stimulation, microstimulation, nerve regeneration through electrical stimulation, temperature sensing, and glucose level monitoring.

Figure 11A:
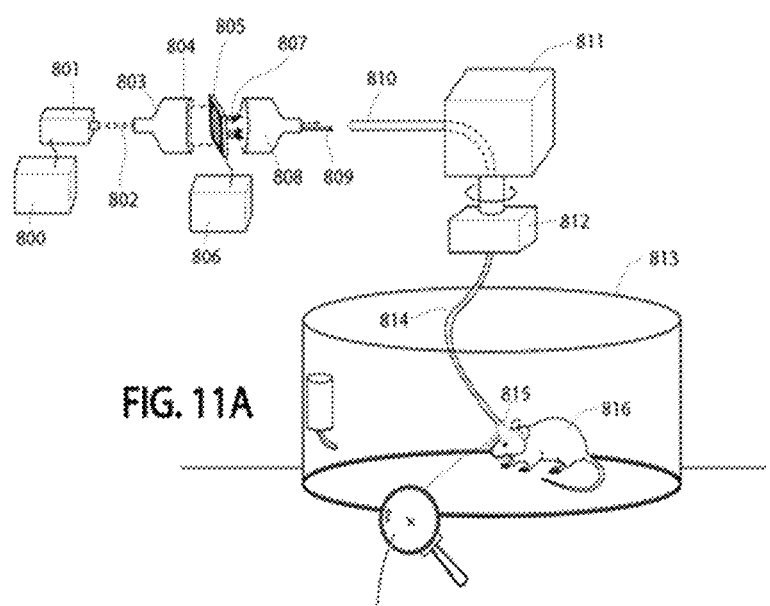
FIG. 11A illustrates an example method of use of the ORS-based implanted electronics to stimulate a mouse brain in-vivo.
Figure 11B:
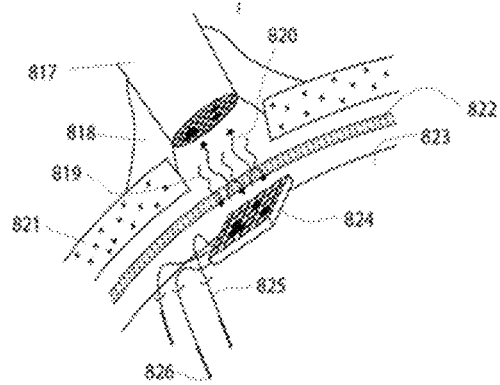
FIG. 11B illustrates a cross-section of the implanted ORS-based device in the skull and the optical component coupling the input and output light.
Figure 11C:
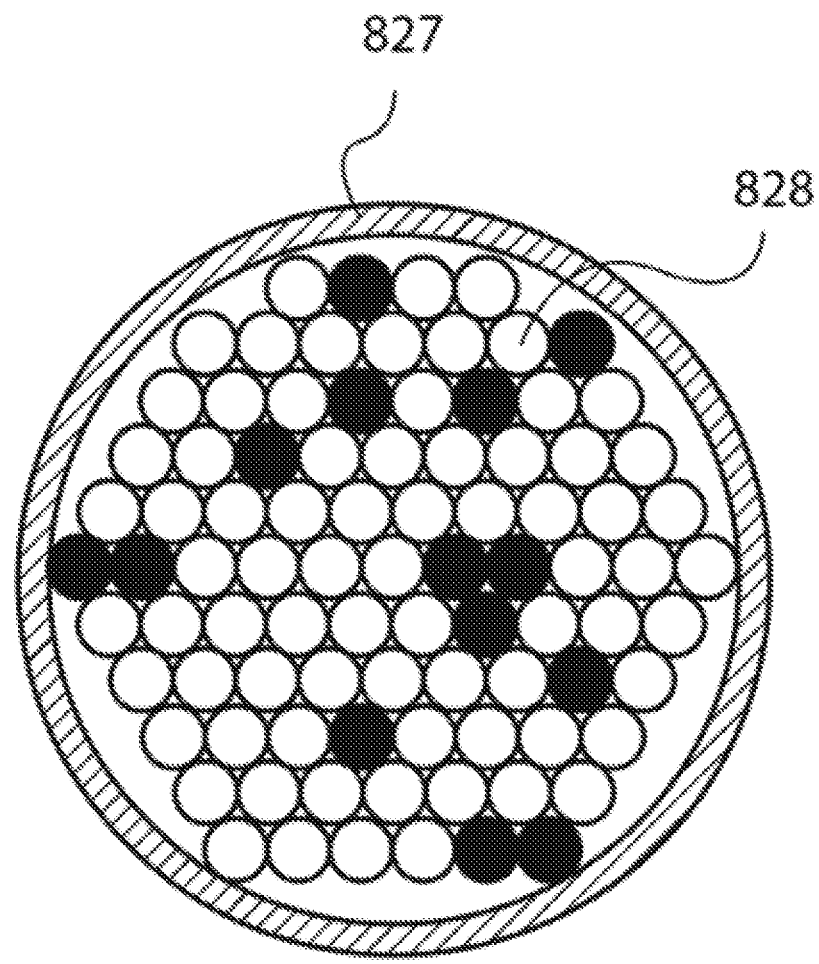
FIG. 11C illustrates a cross-section of the fiber optical bundle with active regions shown with black fill.
Figure 11D:
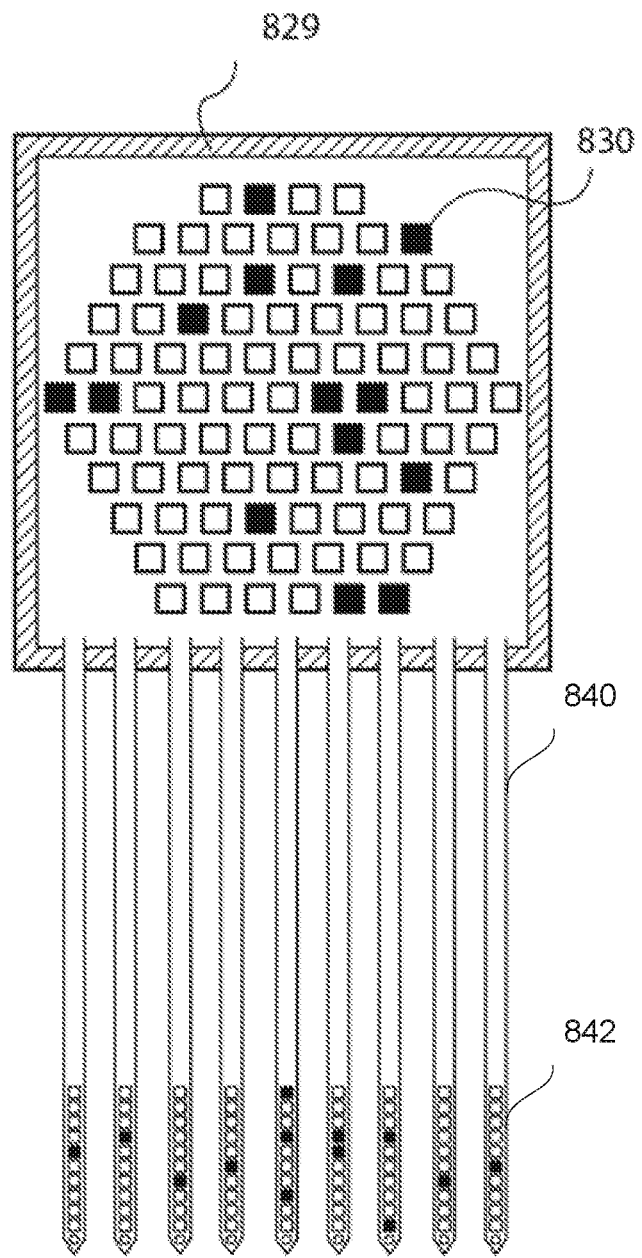
FIG. 11D illustrates the corresponding active sites on an ORS-based device.

FIG. 11A illustrates a method of use of the ORS-based implanted electronics to stimulate a mouse brain in-vivo. A projected is used to pattern light that is passed through an optical element, such as an endoscope, onto the ORS implanted in the living mouse. FIG. 11B illustrates a cross-section of the implanted ORS-based device in the skull and the optical component coupling the input and output light. FIG. 11C illustrates a cross-section of the fiber optical bundle with active regions shown with black fill. FIG. 11D illustrates the corresponding active sites on an ORS-based device.

As shown in FIG. 11A, the ORS-based implantable electronics based on some embodiments of the disclosed technology can be used for stimulation in a living mouse brain. A laser diode 801 produces an un-patterned light beam 802. The light signal in 802 can be modulated at fast speeds, greater than 10 kHz, using the laser diode controller 800. The beam can be expanded through a beam expander 803 with a resulting beam 804 that is passed through an optical display such as a liquid crystal display (LCD) 805 controlled by an external controller 806. The resulting patterned light 807 can be reduced through an inverted beam expander 808 to condense the resulting light 809 into the opening of an endoscope or a first optical fiber optic bundle 810. The fiber optic bundle 810 may pass through an externally controlled commutator 811, 812 allowing for rotation and movement of a second optical fiber bundle 814. The image of the patterned light can be guided to the head of the mouse 816 where an ORS-based implantable electronics 815 is mounted, typically with dental cement.

In some implementations, the ORS-based implantable electronics 815 can include an array of optical elements, a plurality of flexible electrodes and corresponding active electrode areas. Each flexible electrode is mapped to an active electrode area so that the plurality of flexible electrodes can cause biological process in the mouse brain or convey information monitored by a set of active electrode areas coupled to optical elements. The flexible electrodes can be inserted or implanted in different locations in the mouse brain to stimulate different locations in the mouse brain or collect information from different locations in the mouse brain.

A cross-section of the head mount is illustrated in FIG. 11B. The skull 821 of the mouse has a small opening allowing for optical access of the fiber optic bundle 817. The fiber optic bundle 817 may be fixed by a support 818, and input light for the ORS 819 or output light from the ORS 820 is transferred via the optical fiber bundle 817. In this example, no physical connection to the ORS is needed to accomplish multi-channel stimulation.

In some implementations, the ORS 824 may include optical elements and flexible electrodes 825 extending from the ORS 824 can then be inserted into the tissue of the mouse brain 823. This allows the various active exposed areas of the electrodes 826 to be deep into the tissue while the ORS 824 remains at the surface of the mouse brain 823. In some implementations, the optical elements of the ORS 824 include the photovoltaics structured to convert input light into electricity. Sensors engaged to the active exposed areas 826 of the electrodes 825 and responsive to a target substance in the mouse brain may produce an electrical sensor signal indicative of a property of the target substance. The optical elements of the ORS 824 also include light emitters structured to produce output light that is modulated to carry the electrical sensor signal to wirelessly and optically transmit the electrical sensor signal to the remote control and/or monitoring system. Here, the sensors and light emitters can receive power from the electricity generated by the photovoltaics.

In some implementations, the ORS-based device includes an array of optical elements on the ORS 824 and a plurality of flexible electrode ribbons 825 coupled to the array of optical elements on the ORS 824. Each flexible electrode ribbon 825 can include a plurality of active electrode areas 826 that is mapped to the array of optical elements so that information measured by the plurality of active electrode areas 826 can be represented as patterns of activated/deactivated optical elements on the ORS 824.

As shown in FIG. 11C, the fiber optic bundle 817 may include a plurality of optical fibers surrounded by a cladding layer 827. As shown in FIG. 11D, the ORS 824 may include, among others, a plurality of optical elements 830 and an encapsulation layer 829.

As shown in FIG. 11D, the ORS-based device 829 includes an array of optical elements 830 and a plurality of flexible electrode ribbons 840 coupled to the array of optical elements. Each flexible electrode ribbon 840 can include a plurality of active electrode areas 842 that is mapped to the array of optical elements 830 so that information measured by the plurality of active electrode areas 842 can be represented as patterns of activated/deactivated optical elements 830 on the ORS 829. As shown in FIG. 11B, the patterns of activated/deactivated optical elements on the ORS 824 can be optically transmitted to the fiber optic bundle 817, and as shown in FIG. 11C, the patterns can be optically transmitted via the fiber optic bundle 817 to a remote monitoring device (not shown).

Figure 12:
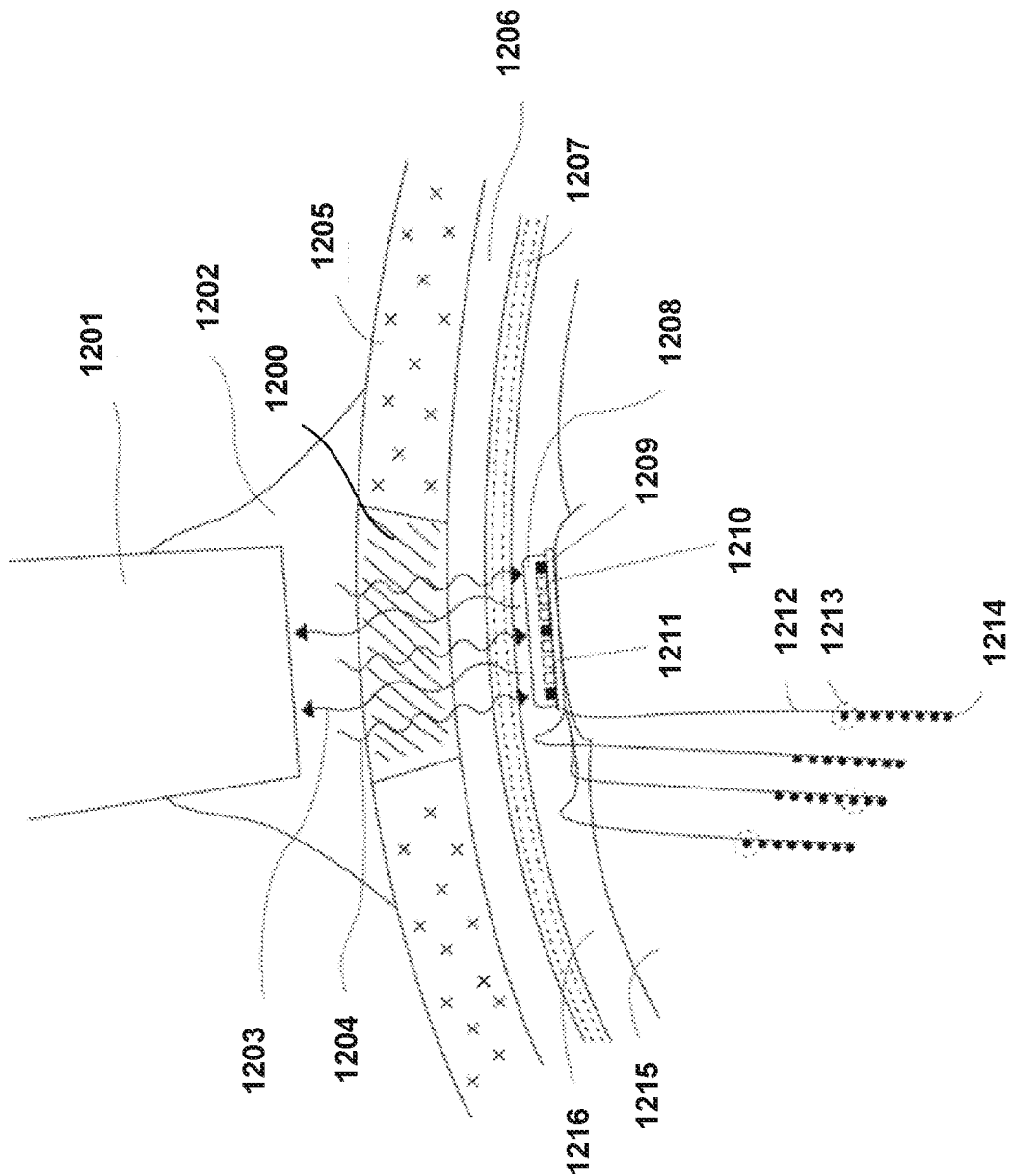
FIG. 12 illustrates a cross-section of an implanted ORS-based device in-vivo where a region of the skull has been replaced with a transparent material.

FIG. 12 illustrates a cross-section of an implanted ORS-based device in-vivo where a region of the skull or a surface of other nerve systems, through which the ORS-based device is implanted, has been replaced with a transparent material 1200. The ORS-based device has no physical contacts to the outside of the skull in this embodiment.

In some implementations, the ORS may include optical elements 1209, 1210 and top and bottom encapsulation layers 1208, 1211. The flexible electrodes 1212 extending from the ORS can then be inserted into the tissue 1206, 1207, 1216. This allows the various active exposed areas of the electrodes 1212 to be deep into the tissue 1206, 1207, 1216 while the ORS remains at the surface of the nervous system 1215 such as brain, muscles and the retina. A fiber optic bundle 1201 may be fixed by a support 1202 so that input light for the optical elements 1209, 1210 or output light from the optical elements 1209, 1210 is transferred via the optical fiber bundle 1201 through the transparent material 1200. In this example, no physical connection to the ORS is needed to accomplish multi-channel stimulation.

In some implementations, the optical elements 1209, 1210 include the photovoltaics structured to convert input light into electricity. Sensors engaged to the active exposed areas 1213, 1214 of the electrodes 1212 and responsive to a target substance in the nervous system 1215 may produce an electrical sensor signal indicative of a property of the target substance. The optical elements 1209, 1210 of the ORS also include light emitters structured to produce output light that is modulated to carry the electrical sensor signal to wirelessly and optically transmit the electrical sensor signal to the remote control and/or monitoring system. Here, the sensors and light emitters can receive power from the electricity generated by the photovoltaics.

As discussed in this patent document, in an embodiment of the disclosed technology, an apparatus includes a plurality of optical elements arranged in an array, each of the plurality of optical elements that are configured to perform conversion between electrical signals and optical signals, and a plurality of electrodes coupled in communication with the plurality of optical elements, each of the plurality of electrodes including an active electrode area coupled to be in communication with one of the plurality of optical elements to stimulate a biological process in a nerve system interacting with the plurality of electrodes based on electrical input signals received by the plurality of electrodes from the optical elements to produce responsive electrical signals and monitor the biological process by transmitting the responsive electrical signals from the plurality of electrodes to the plurality of optical elements which produce optical output signals based on the responsive electrical signals as monitored information. The electrical output signals are converted to patterned light outputs by the plurality of optical elements such that the patterned light outputs in the array indicate a corresponding electrical pattern monitored from the biological process in the nerve system.

In some implementations, the plurality of optical elements includes photovoltaic circuitry configured to generate the electrical input signals based on light incident on the plurality of optical elements. In some implementations, the plurality of optical elements includes light emitting devices configured to generate the optical output signals based on an electrical pattern formed by the responsive electrical signals from the plurality of electrodes caused by the biological process in the nerve system. In some implementations, each of the plurality of optical elements includes one or more light emitting devices to produce one of the optical output signals in response to one or more of the responsive electrical signals, and one or more photovoltaic devices configured to generate electrical power in response to incident light and coupled to supply the generated electrical power to the one or more light emitting devices. In some implementations, each of the plurality of optical elements includes an amplifier circuitry coupled to the one or more light emitting devices and the one or more photovoltaic devices to amplify the generated electrical power from the one or more photovoltaic devices and to apply the amplified electrical power to the one or more light emitting devices.

In some implementations, the apparatus further includes a transceiver structured to electrically or optically connected to the plurality of optical elements to provide power to the plurality of optical elements and the plurality of electrodes and wirelessly communicate with a remote controller or remote monitoring device to relay communication between the plurality of optical elements and the remote controller or remote monitoring device. In some implementations, the transceiver includes a body-mounted device or a wearable device. In some implementations, the array of the plurality of optical elements is structured to allow for the stimulation of the biological process in the nerve system by interacting with a two-dimensional pattern of light incident to the array of the plurality of optical elements. In some implementations, the plurality of electrodes are structured for insertion into biological tissue to deliver electrical input signals to the biological tissue and to receive responsive electrical signals from the biological tissue. In some implementations, In some implementations, the apparatus further includes an encapsulation structure formed to enclose and encapsulate the plurality of optical elements to form a package that is suitable for being implanted into or for interfacing with a biological tissue. In some implementations, the encapsulation structure is structured to be suitable for being implanted into or for interfacing with brain or muscle tissue. In some implementations, the apparatus further includes a plurality of electrical interconnects coupled between the plurality of optical elements and the plurality of electrodes to have one or more lengths that allow the plurality of electrodes to be inserted into tissue at a location that is remote from the plurality of optical elements.

As discussed in this patent document, in another embodiment of the disclosed technology, an apparatus includes a plurality of optical to electrical transducers arranged in a two-dimensional array, wherein each of the plurality of optical to electrical transducers is configured to convert incident light to an electrical signal, a plurality of electrodes, wherein each of the plurality of electrodes is associated with one of the plurality of optical to electrical transducers, wherein the plurality of optical to electrical transducers are configured to cause generation of electrical signals at associated electrodes, respectively, when the plurality of optical to electrical transducers is illuminated by a two-dimensional pattern of incident light so that the generated electrical signals at the associated electrodes are representative of a spatial pattern in the two-dimensional pattern of incident light, and a plurality of electrical interconnects coupled to provide electrical connection between the plurality of electrodes and the plurality of optical to electrical transducers.

In some implementations, a pattern of the electrical pulses is determined by the two-dimensional pattern of light. In some implementations, the plurality of electrodes are structured for insertion into biological tissue to deliver electrical input signals to the biological tissue and to receive responsive electrical signals from the biological tissue. In some implementations, the plurality of electrical interconnects is structured to have one or more lengths that allow the plurality of electrodes to be inserted into tissue at a location that is remote from the plurality of optical to electrical transducers.

As discussed in this patent document, in another embodiment of the disclosed technology, an apparatus includes a plurality of optical to electrical transducers arranged in a two-dimensional array, wherein each of the plurality of optical to electrical transducers is configured to convert incident light to an electrical signal, a plurality of optical sources each operable to emit light as an optical output representing a sensor measurement, wherein each optical to electrical transducer has a corresponding optical source, a plurality of electrodes, wherein each electrode is associated with one or more optical to electrical transducers from the plurality of optical to electrical transducers, wherein each corresponding optical source is configured and coupled to be modulated by a voltage at one of the plurality of electrodes, and a plurality of electrical interconnects coupled to provide electrical connection between the plurality of electrodes and the plurality of optical sources to allow for modulation of optical outputs of plurality of optical sources in response to voltages at the plurality of electrodes to produce the optical output representing the sensor measurement.

In some implementations, the apparatus further includes a camera configured to receive the modulated light from the plurality of optical sources. In some implementations, the plurality of optical sources and the plurality of optical to electrical transducers may be structured such that a two-dimensional pattern of light illuminates the plurality of optical to electrical transducers causing the generation of light at one or more of the plurality of optical sources determined by the two-dimensional pattern of light and one or more voltages at the plurality of electrodes including the voltage. In some implementations, the plurality of electrodes is structured for insertion into biological tissue. In some implementations, the apparatus further includes an encapsulation structure formed to enclose and encapsulate the plurality of optical to electrical transducers, the plurality of optical elements to form a package that is suitable for being implanted into or for interfacing with nerve tissue or muscle tissue. In some implementations, interconnects in the plurality of electrical interconnects have one or more lengths that allow the plurality of electrodes to be inserted into tissue at a location that is remote from the plurality of optical to electrical transducers.

As discussed in this patent document, in an embodiment of the disclosed technology, an apparatus includes a plurality of optical elements arranged in an array, each of the plurality of optical elements being configured to perform conversion between electrical signals and optical signals, and a plurality of electrodes, each of the plurality of electrodes including active electrode areas mapped to at least one of the plurality of optical elements to stimulate a biological process in a nerve system based on electrical input signals received from the optical elements and monitor the biological process to transmit optical output signals as monitored information to the optical element. The electrical output signals are converted to patterned light outputs by the plurality of optical elements such that the patterned light outputs in the array indicate a corresponding electrical pattern monitored from the biological process in the nerve system. In some implementations, the array of optical elements may constitute the optical relay station discussed above.

In some implementations, the plurality of optical elements includes photovoltaics configured to generate the electrical input signals based on light incident on the plurality of optical elements. In some implementations, the plurality of optical elements includes light emitting devices configured to generate the optical output signals based on the electrical pattern monitored from the biological process in the nerve system. In some implementations, the plurality of optical elements includes a single stage optical voltage amplifier including one or more light emitting devices, and one or more photovoltaic devices configured to provide power to the one or more light emitting devices and generate output voltages based on incident light.

In some implementations, the plurality of optical elements is electrically connected to the active electrode areas. In some implementations, the plurality of optical elements is optically connected to a remote controller or remote monitoring device.

In some implementations, the apparatus may further include a transceiver structured to electrically or optically connected to the plurality of optical elements to provide power to the plurality of optical elements and the plurality of electrodes and wirelessly communicate with a remote controller or remote monitoring device to relay communication between the plurality of optical elements and the remote controller or remote monitoring device. In some implementations, the transceiver includes at least one of a body-mounted device or a wearable device.

In some implementations, the stimulation of the biological process in the nerve system is determined by a two-dimensional pattern of light incident of the array of the optical elements.

In some implementations, the plurality of electrodes are inserted into biological tissue. In one example, the biological tissue is nerve tissue or muscle tissue.

In some implementations, the apparatus further includes a plurality of electrical interconnects coupled between the plurality of optical elements and the plurality of electrodes to have one or more lengths that allow the plurality of electrodes to be inserted into tissue at a location that is remote from the plurality of optical elements. In one example, the plurality of electrodes is inserted into a biological tissue, and the plurality of optical elements is placed outside the biological tissue.

As discussed in this patent document, in another embodiment of the disclosed technology, a nerve stimulator apparatus includes a plurality of optical to electrical transducers arranged in a two-dimensional array, wherein each of the plurality of optical to electrical transducers is configured to convert incident light to an electrical signal, a plurality of electrodes, wherein each of the plurality of electrodes is associated with one of the plurality of optical to electrical transducers, wherein the plurality of optical to electrical transducers are configured to generate electrical pulses at the associated electrode upon being illuminated by a two-dimensional pattern of light, and a plurality of electrical interconnects to directly connect each of the plurality of electrodes to the associated one of the one or more of the plurality of optical to electrical transducers.

In some implementations, a pattern of the electrical pulses is determined by the two-dimensional pattern of light. In some implementations, the plurality of electrodes are inserted into biological tissue. In one example, the biological tissue is nerve tissue or muscle tissue.

In some implementations, interconnects in the plurality of electrical interconnects have one or more lengths that allow the plurality of electrodes to be inserted into tissue at a location that is remote from the plurality of optical to electrical transducers.

In another embodiment of the disclosed technology, a nerve sensor apparatus includes a plurality of optical to electrical transducers arranged in a two-dimensional array, wherein each of the plurality of optical to electrical transducers is configured to convert incident light to an electrical signal, a plurality of optical sources, wherein each optical to electrical transducer has a corresponding optical source, a plurality of electrodes, wherein each electrode is associated with one or more optical to electrical transducers from the plurality of optical to electrical transducers, wherein each corresponding optical source is configured to be modulated by a voltage at one of the plurality of electrodes, and a plurality of electrical interconnects to directly connect each of the plurality of electrodes to a control signal configured to modulate an optical output of the corresponding optical source according to the voltage at the one of the plurality of electrodes.

In some implementations, the nerve sensor apparatus further includes a camera configured to receive the modulated light from the plurality of optical sources.

In some implementations, a two-dimensional pattern of light illuminates the plurality of optical to electrical transducers causing the generation of light at one or more of the plurality of optical sources determined by the two-dimensional pattern of light and one or more voltages at the plurality of electrodes including the voltage. In some implementations, a pattern of the pulses is determined by the two-dimensional pattern of light.

In some implementations, the plurality of electrodes are inserted into biological tissue. In some implementations, the biological tissue is nerve tissue or muscle tissue. In some implementations, interconnects in the plurality of electrical interconnects have one or more lengths that allow the plurality of electrodes to be inserted into tissue at a location that is remote from the plurality of optical to electrical transducers.

In this disclosure the term "optical relay station" and "ORS" are used interchangeably referring to the plurality of optical elements, the bottom encapsulation layer, and the top encapsulation layer of the device. The term "flexible electrode" is used to describe a component containing a conductive element than can be bent with a radius of curvature less than 10 mm. The term "flexible electrode" when used in reference to the ORS-based implantable electronics refers to the flexible electrode that extends from the ORS. The term "optical element" is used to refer to an optoelectronic element of that produces light or is powered by light. In reference to the ORS-based implantable electronics, the "optical element" refers to a unit of the plurality of optical elements that composes the ORS. The "optical element" can refer to, for example, a set of photovoltaics wired in series or an optical voltage amplifier. The term "active electrode area" is used to describe a region of the metal interconnect to the optical element that is exposed and not insulated from the outside system. "Wireless" is used to describe a device that does not have electrical interconnects emanating from the device. The electrical interconnects are internal to the device. If a device is said to be a wireless with all dimensions less than 100 microns, there are no electrical interconnects extending outside of the 100 micron boundary bounding the device. The term "patterned light" is used to describe any light that is not of uniform distribution. Patterned light could for example refer to light that has been reflected off of a digital micromirror display with a specified pattern. Un-patterned light is used to refer to light that is of uniform distribution. The light emanating directly from a laser diode would be referred to as "un-patterned." The term "optical stimulator" is used to refer to an optical element that when illuminated with light, causes a change in output voltage producing an electrical pulse. "Optical stimulator" could hence be used to refer to a set of silicon photovoltaics. The term "optical amplifier" or "optical voltage amplifier" or "electrical to optical transducer" is used to describe an optoelectronic circuit that outputs an optical signal indicative of voltage at its inputs. The term "optical biosensor" is used to describe an optoelectronic device that outputs an optical signal indicative of a biologically relevant signal at its inputs, such as, but not limited to, glucose levels, PH, and lactate. The term "biological process" is used describe a process related to a biological function including, but not limited to, a neuron firing, a level of glucose in the body changing, or an increase in cell temperature. The term "GCaMP" is used to refer to the genetically encoded calcium indicator. The term "MOSFET" is used to describe transistors that are metal oxide semiconductor field effect transistors. The term "LED" is used to describe light-emitting diodes. The term "CCD" refers to charge-coupled devices typically found in cameras or detectors. The term "LCD" refers to liquid crystal displays. The term "SLM" refers to spatial light modulators. The term "DMD" refers to digital display micromirrors. The term "SOT" refers to silicon-on-insulator substrates. The term "BOX" refers to the buried oxide layer in an SOT substrate. The term "$SiO_2$" refers to silicon dioxide. The terms "CHF3/O2" and "CHF3/O2 chemistries" are used to describe etching chemistries containing CHF3 or O2 to etch materials. The terms "SU8", "SU-8", and "SU-8 epoxy" are used interchangeably to describe the negative tone photoresist. The term "Pt" refers to platinum. The term "TiN" refers to titanium nitride. The term "PEDOT:PSS" refers to poly(3,4-ethylenedioxythiophene) polystyrene sulfonate. The term "Au" refers to the element gold. The term "DBS" refers to deep-brain stimulation. The term "ECoG" refers to electrocorticography.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data. Computer readable media suitable for storing computer program instructions and data include all forms of nonvolatile memory, media and non-transitory memory devices, including by way of example semiconductor memory devices, e.g., EPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

The disclosed embodiments, the functional operations, and modules described in this document can be implemented in analog or digital electronic circuitry, or in computer software, firmware, or hardware, including the structures disclosed in this document and their structural equivalents, or in combinations of one or more of them. The disclosed embodiments can be implemented as one or more computer program products, i.e., one or more modules of computer program instructions encoded on a non-transitory computer readable medium for execution by, or to control the operation of, a data processing apparatus. The computer readable medium can be a machine-readable storage device, a machine-readable storage substrate, a memory device, a composition of matter effecting a machine-readable propagated signal, or a combination of one or more them. The term "computer" encompasses all apparatuses, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

What is claimed is:

1. An apparatus, comprising:
a plurality of optical elements arranged in an array, each of the plurality of optical elements that are configured to perform conversion between electrical signals and optical signals; and
a plurality of electrodes coupled in communication with the plurality of optical elements, each of the plurality of electrodes including an active electrode area coupled to be in communication with one of the plurality of optical elements to stimulate a biological process in a nerve system interacting with the plurality of electrodes based on electrical input signals received by the plurality of electrodes from the optical elements arranged in the array and mapped to the plurality of electrodes to produce a corresponding pattern of responsive electrical signals and monitor the biological process by transmitting the corresponding pattern of responsive electrical signals from the plurality of electrodes to the plurality of optical elements which produce two-dimensional optical output signals in the array based on the corresponding pattern of responsive electrical signals as monitored information,
wherein the responsive electrical signals are converted to the two-dimensional optical output signals in the array by the plurality of optical elements such that the two-dimensional optical output signals in the array indicate a corresponding electrical pattern monitored from the biological process in the nerve system.

2. The apparatus of claim 1, wherein the plurality of optical elements includes photovoltaic circuitry configured to generate the electrical input signals based on light incident on the plurality of optical elements.

3. The apparatus of claim 1, wherein the plurality of optical elements includes light emitting devices configured to generate the optical output signals based on an electrical pattern formed by the responsive electrical signals from the plurality of electrodes caused by the biological process in the nerve system.

4. The apparatus of claim 1, wherein each of the plurality of optical elements includes one or more light emitting devices to produce one of the optical output signals in response to one or more of the responsive electrical signals, and one or more photovoltaic devices configured to generate electrical power in response to incident light and coupled to supply the generated electrical power to the one or more light emitting devices.

5. The apparatus of claim 4, wherein each of the plurality of optical elements includes amplifier circuitry coupled to the one or more light emitting devices and the one or more photovoltaic devices to amplify the generated electrical power from the one or more photovoltaic devices and to apply the amplified electrical power to the one or more light emitting devices.

6. The apparatus of claim 1, further comprising a transceiver structured to electrically or optically connected to the plurality of optical elements to provide power to the plurality of optical elements and the plurality of electrodes and wirelessly communicate with a remote controller or remote monitoring device to relay communication between the plurality of optical elements and the remote controller or remote monitoring device.

7. The apparatus of claim 6, wherein the transceiver includes a body-mounted device or a wearable device.

8. The apparatus of claim 1, wherein the array of the plurality of optical elements is structured to allow for the stimulation of the biological process in the nerve system by interacting with a two-dimensional pattern of light incident to the array of the plurality of optical elements.

9. The apparatus of claim 1, wherein the plurality of electrodes are structured for insertion into biological tissue to deliver electrical input signals to the biological tissue and to receive responsive electrical signals from the biological tissue.

10. The apparatus of claim 9, further comprising an encapsulation structure formed to enclose and encapsulate the plurality of optical elements to form a package that is suitable for being implanted into or for interfacing with a biological tissue.

11. The apparatus of claim 10, wherein the encapsulation structure is structured to be suitable for being implanted into or for interfacing with brain or muscle tissue.

12. The apparatus of claim 1, further comprising a plurality of electrical interconnects coupled between the plurality of optical elements and the plurality of electrodes to have one or more lengths that allow the plurality of electrodes to be inserted into tissue at a location that is remote from the plurality of optical elements.

13. The apparatus of claim 1, wherein the plurality of optical elements is grouped into a plurality of sub-arrays and the plurality of electrodes is grouped into a plurality of flexible electrode ribbons such that each sub-array of the optical elements is mapped to each electrode in one-to-one correspondence.

14. The apparatus of claim 1, further comprising an optical spatial modulator placed relative to the plurality of optical elements to modulate incident light to carry a spatial pattern when incident onto the plurality of optical elements to generate a pattern in the electrical input signals received by the plurality of electrodes from the optical elements.

15. The apparatus of claim 1, wherein the plurality of optical elements includes:
   a plurality of optical to electrical transducers arranged in a two-dimensional array, wherein each of the plurality of optical to electrical transducers is configured to convert incident light to an electrical signal as one of the electrical input signals received by the plurality of electrodes from the optical elements such that the plurality of optical to electrical transducers convert incident light into the electrical input signals, respectively;
   a plurality of optical sources each operable to emit light as an optical output representing a sensor measurement, wherein each optical to electrical transducer has a corresponding optical source and the plurality of optical sources produce the optical output signals, respectively, based on the responsive electrical signals, respectively, as monitored information;
   a plurality of electrical interconnects coupled to provide electrical connection between the plurality of electrodes and the plurality of optical sources to allow for modulation of optical outputs of plurality of optical sources in response to voltages at the plurality of electrodes to produce the optical output representing the sensor measurement.

16. The apparatus of claim 15, further comprising:
   a camera configured to receive the modulated light from the plurality of optical sources.

17. The apparatus of claim 15, wherein the plurality of optical sources and the plurality of optical to electrical transducers are structured such that a two-dimensional pattern of light illuminates the plurality of optical to electrical transducers causing the generation of light at one or more of the plurality of optical sources determined by the two-dimensional pattern of light and one or more voltages at the plurality of electrodes including the voltage.

18. The apparatus of claim 15, wherein the plurality of electrodes is structured for insertion into biological tissue.

19. The apparatus of claim 15, further comprising an encapsulation structure formed to enclose and encapsulate the plurality of optical to electrical transducers, the plurality of optical sources to form a package that is suitable for being implanted into or for interfacing with nerve tissue or muscle tissue.

20. The apparatus of claim 15, wherein electrical interconnects in the plurality of electrical interconnects have one or more lengths that allow the plurality of electrodes to be inserted into tissue at a location that is remote from the plurality of optical to electrical transducers.

21. The apparatus of claim 1, further comprising a plurality of conductive interconnects, wherein each of the plurality of optical elements comprises an input terminal and an output terminal and each of the conductive interconnects extends from the input terminals or output terminals of the optical elements in a subarray or a column of the array to one or more electrode areas.

22. The apparatus of claim 1, further comprising a plurality of flexible electrode ribbons coupled to the array of optical elements, wherein each flexible electrode ribbon comprises a plurality of electrodes mapped to a plurality of optical elements in the array such that information measured by the plurality of electrodes is represented as a pattern of activation or deactivation of the plurality of optical elements in the array.

23. The apparatus of claim 22, further comprising an opening in each of the plurality of flexible electrode ribbons.

24. The apparatus of claim 23, wherein the opening is at the end of the flexible electrode ribbon and configured to allow a protruding portion of a probe to pass through to facilitate inserting or implanting the flexible electrode ribbon into a tissue.

* * * * *